(12) United States Patent
Svanborg et al.

(10) Patent No.: US 11,752,192 B2
(45) Date of Patent: Sep. 12, 2023

(54) INHIBITOR OF RNA POLYMERASE II

(71) Applicant: SELECTIMMUNE PHARMA AB, Lund (SE)

(72) Inventors: Catharina Svanborg, Malmo (SE); Nina Filenko, Lund (SE); Ines Ambite, Lund (SE)

(*) Notice: Subject to any disclaimer, the term of this patent is extended or adjusted under 35 U.S.C. 154(b) by 0 days.

(21) Appl. No.: 17/032,308

(22) Filed: Sep. 25, 2020

(65) Prior Publication Data
US 2021/0069291 A1    Mar. 11, 2021

Related U.S. Application Data

(62) Division of application No. 16/341,962, filed as application No. PCT/IB2017/056413 on Oct. 16, 2017, now abandoned.

(30) Foreign Application Priority Data

Oct. 17, 2016 (GB) .................................. 1617548

(51) Int. Cl.
*A61K 38/16* (2006.01)
*A61K 35/74* (2015.01)
*G01N 33/573* (2006.01)
*A61K 38/44* (2006.01)

(52) U.S. Cl.
CPC ............ *A61K 38/164* (2013.01); *A61K 35/74* (2013.01); *A61K 38/443* (2013.01); *G01N 33/573* (2013.01); *G01N 2333/91255* (2013.01); *Y02A 50/30* (2018.01)

(58) Field of Classification Search
None
See application file for complete search history.

(56) References Cited

U.S. PATENT DOCUMENTS

| | | |
|---|---|---|
| 2004/0082040 A1 | 4/2004 | Rieping et al. |
| 2010/0047861 A1 | 2/2010 | Hara et al. |
| 2014/0194483 A1 | 7/2014 | Dervan et al. |
| 2016/0220687 A1 | 8/2016 | Alhamdan |
| 2019/0240287 A1* | 8/2019 | Svanborg ............... A61P 13/00 |
| 2021/0069291 A1* | 3/2021 | Svanborg ............... A61P 13/00 |

FOREIGN PATENT DOCUMENTS

| | | | |
|---|---|---|---|
| WO | 2016/193939 A1 | 12/2016 | |
| WO | 2018/073725 A1 | 4/2018 | |
| WO | WO-2018073725 A1 * | 4/2018 | ........... A61K 38/443 |

OTHER PUBLICATIONS

AMbite et al, J Clin Invest. 2021;131(4):e140333. https://doi.org/10.1172/JCI140333. published online:Feb. 15, 2021 (Year: 2021).*

Agace et al., "Interleukin-8 and the Neutrophil Response to Mucosal Gram-negative Infection", Journal of Clinical Investigation, 1993, pp. 780-785, vol. 92.
Ambite et al., "Bacterial Suppression of RNA Polymerase II-Dependent Host Gene Expression", Pathogens, 2016, pp. 1-11, vol. 5.
International Search Report and Written Opinion for International Application No. PCT/IB2017/056413, dated Jan. 22, 2018; 19 pgs.
Koves et al., "Rare Emergence of Symptoms during Long-Term Asymptomatic *Escherichia coli* 83972 Carriage without an Altered Virulence Factor Repertoire", The Journal of Urology, 2014, pp. 519-528, vol. 191.
Lindberg et al., "Asymptomatic bacteriuria in schoolgirls", The Journal of Pediatrics, 1978, pp. 194-199, vol. 92, No. 1.
Lutay et al., "Bacterial control of host gene expression through RNA polymerase II", The Journal of Clinical Investigation, 2013, pp. 2366-2379, vol. 123, No. 6.
NCBI Reference Sequence NC_017631.1, "*Escherichia coli* ABU 83972, complete genome", https:/www.ncbi.nlm.nih.gov/nuccore/386637352, dated Jul. 10, 2019; 2 pgs.
Search Report from GB Application No. GB1617548.1, dated Jul. 26, 2017; 4 pgs.
Sunden et al., "Deliberately induced *E. coli* 83972 bacteriuria protects against recurrent lower urinary tract infections in patients with incomplete bladder emptying. A blinded randomized placebo-controlled cross-over study", Lund University Publications, author-produced version of paper published in The Journal of Urology, May 16, 2010; 24 pgs.
Uehara et al., "Daughter cell separation is controlled by cytokinetic ring-activated cell wall hydrolysis", The EMBO Journal, 2010, pp. 1412-1422, vol. 29, No. 8.
Wullt et al., "P fimbriae enhance the early establishment of *Escherichia coli* in the human urinary tract", Molecular Microbiology, 2000, pp. 456-464, vol. 38, No. 3.
Yu et al., "RNA polymerase II-associated factor 1 regulates the release and phosphorylation of paused RNA polymerase II", Science, 2015, pp. 1383-1386, vol. 350, No. 6266.
Office Action from U.S. Appl. No. 16/341,962, dated Jun. 25, 2020; 13 pgs.

* cited by examiner

*Primary Examiner* — Brian Gangle
(74) *Attorney, Agent, or Firm* — Polsinelli PC; Christine M. Emnett

(57) ABSTRACT

An inhibitor of RNA polymerase II is described, wherein said inhibitor is selected a moiety which targets a protein selected from cyclin kinase 12 (CDK12) or its recruiting protein PAF1C. Particular examples of such inhibitors are polypeptides expressed by a gene selected from IldD, IldR, nlpD or rfaH of a bacterial species, such as a commensal bacteria or asymptomatic carrier, or a variant of said protein. Inhibitors may be based upon bacterial Sigma S or NplD proteins. These inhibitors are useful in therapies, to suppress protein expression. Thus they may be used as immunosuppressants, anti-inflammatory or anti-infection agents.

15 Claims, 21 Drawing Sheets

Specification includes a Sequence Listing.

Figure 2B

| no acid change | Gene |
|---|---|
| Ala81Val | cysE |
| Val72Gly | ECABU_c03060 |
| Ala37Thr | phrB |
| Thr322Ala | ybjD |
| Arg227Cys | ssuD |
| Ala39Val | ECABU_c11750 |
| Tyr463Cys | mdoH |
| Ala124Thr | mdtK |
| Gln58Arg | ECABU_c23200 |
| Ile106Asn | rcsB |
| Thr18Ala | lrhA |
| Tyr52Cys | hisQ |
| Ile400Val | eutB |
| Tyr174Cys | atpD |
| Lys959Arg | rpoC |
| Lys79Thr | mutL |
| Tyr209His | nlpD |
| Pro52Leu | rfaH |
| Lys139fs | citC |
| Gly200fs | ydiV |
| Gly445fs | astB |
| Thr271fs | atoB |
| Gly336fs | ygfQ |
| Glu22fs | lldR |
| Gly27fs | lldD |

Figure 2C

| Genes mutated in SN25 | Function |
|---|---|
| nlpD | Lipoprotein, regulator of amidase (cell wall hydrolase) with a potential function in cell wall formation. Gene located in an operon with the rpoS gene, which encodes a subunit of E. coli RNA polymerase (Sigma S). |
| lldD | Enzyme that catalyzes the conversion of L-lactate to pyruvate in the aerobic L-lactate metabolism. |
| lldR | Regulator of the lldPRD operon, involved in L-lactate metabolism. |
| rfaH | Transcriptional anti-terminator, required for efficient expression of UPEC long chain LPS and hemolysin. Affects biofilm formation, loss attenuates virulence. |
| cysE | Serine acetyltransferase, catalyzes the conversion of L-serine to O-acetyl-L-serine. Affects biofilm formation in E. coli K-12. |
| lrhA | Regulator of flagella, motility and chemotaxis genes. |
| mdoH | Negative regulator of colanic acid capsular polysaccharide. |
| rcsB | Positive regulator of colanic capsule biosynthesis. |

INHIBITOR OF RNA POLYMERASE II

CROSS-REFERENCE TO RELATED APPLICATIONS

This application is a divisional of U.S. application Ser. No. 16/341,962, filed Apr. 15, 2019, which is a U.S. National Stage Application of International Application No. PCT/IB2017/056413, filed Oct. 16, 2017, which claims the benefit of, and priority to, Great Britain Patent Application No. 1617548.1, filed Oct. 17, 2016, the entire contents of which are hereby incorporated by reference in their entirety.

SEQUENCE STATEMENT

This application contains a Sequence Listing that has been submitted in ASCII format via EFS-Web and is hereby incorporated by reference in its entirety. The ASCII copy, created on Oct. 17, 2016, is named P3377_Sequence_listing.txt, and is about 10,000 bytes in size.

FIELD OF THE INVENTION

The present invention relates to factors and moieties that can modulate host protein expression, for example, a factor having immunosuppressant activity, to methods of preparing the factors and moieties and to their use in therapy.

BACKGROUND TO THE INVENTION

The multi-subunit RNA polymerase II complex (Pol II) is essential for protein expression in eukaryotes. Transcription cycle has been extensively characterized to show that around 10% of all expressed genes are involved in transcriptional regulation, assembly and control of the Pol II complex. In eukaryotic cells, RNA polymerase II catalyzes the synthesis of mRNA and small nuclear RNA. Pol II transcription cycle consists of several stages, termed preinitiation, initiation, promoter clearance, during which Pol II pauses at the promoter proximal site, followed by escape from pausing, productive elongation and termination.

For specificity, the assembly of Pol II is tightly controlled and the efficiency of transcription is modified at individual promoters by activators and repressors, as well as general or specific transcription factors. The carboxy-terminal domain (CTD) of the largest Pol II subunit, Rpb1, contains a heptamer sequence Tyr1-Ser2-Pro3-Thr4-Ser5-Pro6-Ser7 repeated 52 times in mammalian cells. During the transcription cycle, CTD is subject to continuous structural remodeling by kinases and phosphatases and serves as a platform for binding and release of numerous regulatory proteins. The recruitment of Ser2-specific kinase activity in the form of positive transcription elongation factor b (P-TEFb) is regarded to be a critical step in the activation of promoter-proximally paused Pol II, facilitating its release from pause sites. P-TEFb is composed of cyclin-dependent kinase 9 (CDK9) and its regulatory cyclin T1. The more recently discovered Cdk12 phosphorylates CTD of RNA polymerase in the middle and 3' end of genes. P-TEFb is a general transcription factor required for efficient expression of most cellular genes, therefore, its activity is accurately mediated with positive regulator bromodomain protein Brd4, and negative regulators noncoding 7SK snRNA and the HEXIM1 protein. It was shown that P-TEFb recruits PAF1 to Pol II complex, which is followed by CDK12 recruitment by PAF1 (Yu et al., Science 2015. 350(6266:1383-6). Dephosphorylation of Ser2-phosphates is done by phosphatases FCP1 (TFIIF-dependent CTD phosphatase 1) and Cdc14.

The host Pol II transcription machinery is targeted by bacteria, as first described for *Escherichia coli* strains that establish an asymptomatic carrier state in the human urinary bladder (Lutay et al., J. Clin Invest. 2013, 123(6) 2366-79). Asymptomatic bacteriuria (ABU) actively modifies the host response by inhibiting Pol II dependent transcription, including pathology-generating signaling pathways in the host (Lutay et al., 2013 supra.). In 24 hours after human inoculation with the prototype ABU *E. casumoli* strain 83972, more than 60% of all genes were suppressed; this inhibition was verified by infection of human cells. Among different ABU strains (n=75), 37% were strongly inhibitory compared to 17% of APN strains (n=88). The symbiotic relationship between ABU strains and their hosts is also influenced by a lack of virulence factors, resulting from virulence gene attenuation in these strains.

These findings indicate that suppression or inhibition of RNA polymerase II may be an effective method for modulating the immune system, in particular by acting as modulators of gene expression. There is frequently a need to modulate gene expression, in particular of the immune system either by stimulation or suppression in connection with a wide variety of therapeutic applications.

Immunosuppressants are required in a wide a variety of therapies. This includes for instance, the prevention of rejection of transplanted organs or tissues such as bone marrow, heart, kidney or liver, the treatment of autoimmune diseases such as rheumatoid arthritis, multiple sclerosis, myasthenia gravis, lupus, sarcoidosis, Crohn's disease, pemphigus and ulcerative colitis.

However, as a broad spectrum suppressor of protein expression, Pol-II inhibitors may find application in any therapy where host protein is over-expressed or problematic. Thus Pol-II inhibitors may also be used in the treatment of inflammatory disease such as asthma, or in the treatment of auto-inflammatory disease such as Behcet's disease, FMF, NOMID, TRAPS or DIRA. It has also been suggested that host-directed immunomodulatory therapies can be used in the treatment of infections, whereby natural mechanisms in the host are exploited to enhance therapeutic benefit. In this case, the objective is to initiate or enhance protective anti-microbial immunity while limiting inflammation-induced tissue injury. Such a mechanism may help to address the increase or antimicrobial resistance as bacteria become resistant to conventional antimicrobial drugs over time.

Earlier attempts to characterize the mechanism of Pol II inhibition by the ABU by comparison of whole genome sequences of *E. coli* 83972 and the uropathogenic strain, *E. coli* CFT073 have failed to identify specific factors associated with this (I. Amibite et al. Pathogens, 2016, 5, 49; doi:10.3390), indicating that this is not a simple matter.

However, as a result of the serendipitous occurrence of attenuated Pol II inhibitory activity in a re-isolate, obtained from a patient inoculated with a prototype ABU, the applicants have been able to make a significant breakthrough in identification of the factors which may be useful in immunosuppression.

SUMMARY OF THE INVENTION

According to a first aspect of the invention, there is provided an inhibitor of host RNA polymerase II (pol II inhibitor) for use in therapy, wherein said inhibitor is a moiety which targets a protein selected from PAF or CDK12.

Moieties which target these proteins may be known in the art or may be identified or designed using conventional screening methods. They may for example comprise antibodies or binding fragments thereof, aptamers or small molecules, which bind to CDK12 or PAF1C so as to inhibit RNA polymerase II in a host cell.

Specific examples of such moieties may be obtained from bacteria, such as the commensal bacteria or asymptomatic carriers such as asymptomatic bacteriuria.

As a result of the isolation of a spontaneous, loss of function mutant of the ABU strain *E. coli* 83972, the applicants have identified bacterial proteins able to act as direct inhibitors Pol II phosphorylation in infected hosts. Mutations were localized by comparative genome sequencing of the *E. coli* 83972 WT and mutant strain and identified sequence variants were systematically introduced into the *E. coli* 83972 WT strain for analyses of effects on Pol II phosphorylation.

In a particular embodiment, the inhibitor is a polypeptide expressed by a gene selected from IldD, IldR, nlpD or rfaH of a bacterial species, or a variant of said polypeptide.

The TATA box binding protein Sigma S was shown to bind human TATA box DNA and to competitively inhibit the binding of human TBP, thus incapacitating the Pol II pre-initiation complex. Furthermore, NlpD, which regulates Sigma S expression, stimulated the degradation of PAF1C, which recruits the kinase CDK12 to the Pol II phosphorylation complex. Both proteins entered host cells. The results identify a novel mechanism used by bacteria to regulate fundamental host cell functions, such as the transcriptional activity at sites of infection.

In a particular embodiment, the inhibitor is a bacterial Sigma S protein or a variant thereof, or an active fragment of either of these. An example of such a protein is SEQ ID NO 2 or a truncated form of SEQ ID NO 2.

(SEQ ID NO 1)
MSQNTLKVHDLNEDAEFDENGVEVFDEKALVEQEPSDNDLAEEELLSQGA

TQRVLDATQLYLGEIGYSPLLTAEEEVYFARRALRGDVASRRRMIESNLR

LVVKIARRYGNRGLALLDLIEEGNLGLIRAVEKFDPERGFRFSTYATWWI

RQTIERAIMNQTRTIRLPIHIVKELNVYLRTARELSHKLDHEPSAEEIAE

QLDKPVDDVSRMLRLNERITSVDTPLGGDSEKALLDILADEKENGPEDTT

QDDDMKQSIVKWLFELNAKQREVLARRFGLLGYEAATLEDVGREIGLTRE

RVRQIQVEGLRRLREILQTQGLNIEALFRE (SEQ ID NO 2)
MFRQGITGRSHLMSQNTLKVHDLNEDAEFDENGVEVFDEKALVEEEPSDN

DLAEEELLSQGATQRVLDATQLYLGEIGYSPLLTAEEEVYFARRALRGDV

ASRRRMIESNLRLVVKIARRYGNRGLALLDLIEEGNLGLIRAVEKFDPER

GFRFSTYATWWIRQTIERAIMNQTRTIRLPIHIVKELNVYLRTARELSHK

LDHEPSAEEIAEQLDKPVDDVSRMLRLNERITSVDTPLGGDSEKALLDIL

ADEKENGPEDTTQDDDMKQSIVKWLFELNAKQREVLARRFGLLGYEAATL

EDVGREIGLTRERVRQIQVEGLRRLREILQTQGLNIEALFRE

As used herein, the term 'fragment' refers to any portion of the given amino acid sequence which will shows Pol II inhibitory activity. Fragments may comprise more than one portion from within the full-length protein, joined together. Portions will suitably comprise at least 5 and preferably at least 10 consecutive amino acids from the basic sequence.

Suitable fragments will include deletion mutants comprising at least 10 amino acids, for instance at least 20, more suitably at least 50 amino acids in length or analogous synthetic peptides with similar structures. They include small regions from the protein or combinations of these.

In a particular embodiment, the fragment will be a peptide which inhibits binding of TBP to Sigma S, for example a fragment comprising amino acids 149-183 of SEQ ID NO 2, shown in bold type in the above sequence, which forms SEQ ID NO 3.

Certain such pol II inhibitors will be novel and these form a further aspect of the invention.

They may be used in a range of therapeutic applications as discussed above, to suppress protein expression. In particular, they may be used as immunosuppressant, anti-inflammatory or anti-infection (such as antibacterial) agents.

The expression "variant" refers to proteins or polypeptides having a similar biological function but in which the amino acid sequence differs from the base sequence from which it is derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions are possible provided that these do not interrupt the function of the DNA binding domain polypeptides. Broadly speaking, fewer non-conservative substitutions will be possible without altering the biological activity of the polypeptides. Determination of the effect of any substitution (and, indeed, of any amino acid deletion or insertion) is wholly within the routine capabilities of the skilled person, who can readily determine whether a variant polypeptide retains the fundamental properties and activity of the basic polypeptide. For example, when determining whether a variant of the polypeptide falls within the scope of the invention, the skilled person will determine whether complexes comprising the variant retain biological activity (e.g. tumour cell death) of complexes formed with unfolded forms of the native protein and the polypeptide has at least 60%, preferably at least 70%, more preferably at least 80%, yet more preferably 90%, 95%, 96%, 97%, 98%, 99% or 100% of the native protein.

Variants of the polypeptide may comprise or consist essentially of an amino acid sequence with at least 70% identity, for example at least 75%, 80%, 85%, 90%, 91%, 92%, 93%, 94%, 96%, 97%, 98% or 99% identity to a native polypeptide sequence. The level of sequence identity is suitably determined using the BLASTP computer program with the native polypeptide sequences as the base sequence. This means that native polypeptide sequences form the sequence against which the percentage identity is determined. The BLAST software is publicly available, for example at the National Library of Medicine's National Center for Biotechnology Information (NCBI) web site (ncbi.nlm.nih.gov).

In a particular embodiment, the inhibitor is a polypeptide expressed by a gene selected from IldD, IldR, nlpD or rfaH of a bacterial species. The bacterial species is suitably a commensal bacteria or an asymptomatic carrier such as asymptomatic bacteriuria (ABU). In particular, the bacteria is an *E. coli* strain, such as *E. coli* 83972.

In a particular embodiment also, the inhibitor is a polypeptide expressed by an IldD, Ildr or nldD gene and secreted by the bacteria.

In some embodiments, the inhibitor is of low molecular weight for instance less than 3 kDa. It is suitably resistant to Proteinase K.

In other embodiments, the inhibitor is a larger protein, for example of about 40 kDa.

Such inhibitors may be obtained by culturing the bacteria in an appropriate culture medium such as RPMI. RNA polymerase II activity, which may be tested using appropriate testing methods such as those exemplified hereinafter, may be found in the supernatant, suggesting that the factor responsible is secreted by the bacteria. Suitably the supernatant is separated from the bacteria for example using centrifugation as a preliminary step and then subjected to analysis to confirm RNA polymerase II inhibitor activity. Filtration of the supernatant for example using centrifugal or flow-through filters suitable for separating proteins can be used to remove non-active fractions which tend to be high molecular weight components, thus concentrating the inhibitor activity.

The inhibitor may be purified from the concentrate using conventional methods and the amino acid sequence determined, also using conventional methods. When this has been done, the inhibitor may be produced synthetically, for example using recombinant DNA technology.

For use in modulating the immune system, the pol II inhibitor of the invention is suitably formulated into a pharmaceutical composition in which it is combined with a pharmaceutically acceptable carrier. Such compositions form a further aspect of the invention.

The composition may be in a form suitable for oral administration, for example as a tablet or capsule, for parenteral injection (including intravesical, intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

Methods of using the RNA polymerase II inhibitor will depend upon a variety of factors such as the disease being treated and the nature of the particular inhibitor being used. These will be determined in accordance with clinical practice.

In yet a further aspect, the invention provides a method of treating a patient in need therefore with an effective dosage of an inhibitor of RNA polymerase II as described above. Suitable dosages will be determined in accordance with normal clinical practice, but will generally be in the range approximately from 0.01 mg/kg to 25 mg/kg but with considerable variation between individuals and disease conditions.

As reported hereinafter, the mechanism of Pol II inhibition by the ABU strain was further investigated, but using re-isolates of the prototype ABU strain from inoculated patients, which were screened for attenuation of Pol II inhibitory activity. An attenuated re isolate SN25, was subjected to whole genome sequencing and genomic differences between the ancestor and progeny were identified. The variant positions in the chromosome were subsequently mutated in *E. coli* 83972, by homologous recombination and the mutants were screened for effects on Pol II Ser 2 phosphorylation. The genes lldD and lldR, whose products are involved in aerobic L-lactate metabolism, were shown to significantly affect Pol II phosphorylation. To confirm these effects, a biochemical approach was used. Supernatant of bacteria incubated in tissue culture medium were shown to contain inhibitory activity and was further fractionated to define the molecules responsible for these effects. Weak acids of <3 kD molecular weight, formic and acetic, were identified to have inhibitory effect of Pol II phosphorylation. In addition, Pol II phosphorylation was affected by deletion of nlpD, which encodes a lipoprotein with a potential function in cell wall formation and rfaH and cysE with products of both genes involved in biofilm formation.

In particular, the applicants have identified a new mechanism by which bacterial proteins disturb the formation of the Pol II complex and attenuate the Pol II activation in human cells. The bacterial TATA box binding protein, encoded by rpoS and its transcriptional regulator Nlpd as bacterial genes responsible for this effect through competitive inhibition of the human TATA box binding protein TBP and a reduction in PAF1C, CDK 9 and CDK12. The findings define a new, potent mechanism for cross-regulation of the transcriptional machinery between eukaryotic and prokaryotic cells. Without being bound by theory, the findings may illustrate a new general mechanism of bacterial adaptation and survival in infected hosts.

The encounters between bacteria and host cells are guided by specific molecular interactions. Pathogen attack is often executed by virulence factors via receptor-mediated interactions, involving conserved receptors like the TLRs and pathogen specific recognition mechanisms with specificity for unique sets of virulence factors. Adhesive interactions determine the tissue specificity and site of infection. Exotoxins bind cell surface receptors, such as GM1 (cholera toxin) or Gb3 (Shiga toxin) and after internalization, the toxins interfere with key cellular functions. Endotoxins activate TLR4 signaling cascades and by engaging specific co-receptors, virulence factors determine adaptor protein usage and transcription factor recruitment. Here we propose that bacteria export molecules that enter host cells and attenuate the transcriptional machinery, by competing with molecules involved in the assembly of the Pol II complex and its phosphorylation at Ser2.

As described herein, two, closely related genes have been identified in the WT strain *E. coli* 83972, based on a screen for "loss of function" mutants. A Tyr209Hi amino acid change in NlpD, abolished the inhibitory effect on Pol II phosphorylation. NlpD is a secreted protein with a 25 aa-signal sequence and potential signal peptidase cleavage site and is transported to the bacterial periplasm. NlpD together with other LytM (lysostaphin)—domain-containing factors is required for septal proteoglycan splitting and daughter cell separation. When overexpressed, nlpD changes bacterial morphology, due to the activation of the cell wall hydrolase AmiC. The mutation in SN25 appeared to be located within the AmiC binding site, suggesting that this mutant has lost the ability to activate AmiC and thus to facilitate the secretion of bacterial components and their interactions with the host cell. The rapid reduction in PAF1C and CDK12 protein levels suggested that host proteases or ubiquitinases might be activated. Uehara et al., 2010 discuss four possible mechanisms of bacterial amidase activation by LytM factors including NlpD. These include 1) allosteric or 2) covalent modification (e.g. proteolytic processing) of amidases by the LytM factors, 3) facilitated substrate association of the amidases and 4) prior deformation or hydrolysis of bonds in the PG substrate. Therefore, similarly to activation of the amidase in bacterial cells, NlpD might activate some other enzymes in the host cells.

human TBP for binding to TATA box DNA. By dislodging TBP from its binding site, RpoS may thus prevent pre-initiation complex formation and therefore the binding of Pol II to specific promoters. A general effect on gene expression is supported by a clinical study, showing reduced expression of >60% of all genes in circulating blood cells in patients inoculated with *E. coli* 83972. Despite the inhibition of a large number of genes, effects were much less pronounced than when a pharmacological inhibitor was used, however, suggesting specificity. In eukaryotic promoters, PIC formation and binding of general transcription factor II B (TFIIB) recruits Pol II to the promoter. II B (TFIIB) consists of 4 functional domains—N-terminal Zn ribbon, B reader, B linker and Core domain. Core domain in eukaryotes is required to stabilize the TBP-DNA complex and the Zn ribbon recruits RNA Pol II.

Amino acid analysis reveals that Sigma S shows homology to the core domain of TFIIB (38% over the stretch of 35 AA) but no homology with the Zn ribbon, potentially explaining why Sigma S binds DNA but fails to recruit

```
The NlpD protein is of SEQ ID NO 4:
                                                             (SEQ ID NO 4)
   1 msagspkftv rriaalslvs lwlagcsdts nppapvssvn gnapantnsg mlitpppkmg 61 ttstaqqpqi qpvqqpqiqa tqqpqiqpmq pvaqqpvqme ngrivynrqy gnipkgsysg 121 stytvkkgdt lfyiawitgn dfrdlaqrnn iqapyalnvg qtlqvgnasg tpitggnait 181 qadaaeqgvv ikpaqnstva vasqptitys essgeqsank mlpnnkptat tvtapvtvpt 241 asttepivss tststpistw rwptegkvie tfgaseggnk gidiagskgq aiiatadgrv 301 vyagnalrgy gnliiikhnd dylsayahnd tmlvreqqev kagqkiatmg stgtsstrlh 361 feirykgksv nplrylpqr
```

Interestingly, NlpD is homologous to a human protein, the membrane-spanning 4-domains protein, subfamily A, member 15. A putative role of the membrane-spanning 4-domains protein based on data-mining is signal transduction by being a component of a multimeric receptor complex (human gene database (GeneCards). Homologous region is located towards N-terminus of NlpD (amino acids 44-90) with homology and similarity averaging 37% and 53%, respectively. This might provide some mechanistic explanation of NlpD being potentially inserted into membrane of the host cell before reaching its targets inside the cell.

NlpD also exerts its effect through transcriptional control of rpoS and rpoS-dependent genes. The transcription of rpoS is regulated from a common nlpD promoter and from additional sites within the nlpD ORF. Sigma S is an important regulator of more than 20 stationary phase genes and operons such as genes required for multiple-stress resistance. In addition, as NlpD and Sigma S proteins are encoded by the same gene cluster and are derived from the same polycystronic RNA, direct interactions cannot be excluded. It can be hypothesized that NlpD allosterically modifies Sigma S, facilitating its transport and rendering it active in binding and melting of host cell DNA.

In a particular embodiment, the inhibitor comprises a bacterial NplD protein, or a variant thereof, or an active fragment of either of these. Examples of such proteins are of SEQ ID NO 4.

Without being bound by theory, it is possible that disruption of the pre-initiation complex by Sigma S might be a key step, affecting downstream transcriptional activity. The applicants have shown that bacterial RpoS competes with eukaryotic Pol II. The findings suggest an interesting evolutionary model, where maintaining the basic organization of gene expression and Pol II machinery constituents from bacteria to humans offers a mechanism for coordinate regulation of gene expression between eucaryotes and procaryotes.

To summarize, the applicants obtained a set of data supporting the hypothesis that both bacterial proteins NlpD and Sigma S are internalized by the human host cells. These include experiments on whole cell lysates of cells infected with ABU, co-immunoprecipitation of Pol-II, Sigma S and Nlp D, as well as immunofluorescence studies of ABU infected kidney cells (FIGS. 6A-6D). With immunofluorescence, some background staining is observed for NlpD and RpoS in uninfected control, which might be explained by the relative homology between NlpD and RpoS with some human proteins. NlpD is homologous to human protein, membrane-spanning 4-domains subfamily A member 15 (with 37% homology and 53% similarity over the stretch of 47 amino acids) as well to human protein GREB1-like protein isoform X4, Growth Regulation By Estrogen In Breast Cancer 1 (25% homology and 40% similarity, 116 AA). Likewise, Sigma S is homologous to two human proteins, circulating B cell antibody heavy chain variable region (31% homology and 54% similarity, 45 AA) and as discussed earlier to transcription factor II B (38% homology and 48% similarity, 35 AA).

BRIEF DESCRIPTION OF THE DRAWINGS

The invention will now be particularly described by way of example with reference to the accompanying Figures in which:

FIG. 1A Cells were infected in suspension, labelled for Pol II-Ser2 with fluorescently labeled AB and run on cell flow cytometer. The distribution of phosphorylated Pol II fluorescence was analyzed. Infection with the AU strain decreases host Pol II phosphorylation; FIG. 1B Pol II phosphorylation in control and ABU infected cells, visualized by laser-scanning, slides were mounted and imaged. Nuclei were counterstained with DRAQ5 and fluorescence intensity was quantified by ImageJ software 1.46r. FIG. 1C Mean value of Pol II phosphorylation in ABU infected cells and uninfected control cells. One representative experiment is shown, measured with flow cytometry as shown in A and one was quantified by confocal microscopy, using ImageJ software 1.46r. Means of two experiments. FIG. 1D-F shows how a particular re-isolate, designated SN25, has lost the inhibitory effect on RNA Pol II phosphorylation. FIG. 1D presents flow cytometry, FIG. 1E shows microscopy, FIG. 1F quantitates the results. Results show loss of Pol II phosphorylation repression by reisolate strain SN25 as compared to ancestor strain 83972 in FIG. 1A-C. Error bars show standard error of the mean. FIG. 1G Hit map of gene expression after infection with both strains shows 465 genes upregulated and 385 genes downregulated in both ABU and SN25, 224 genes downregulated only by ABU and 2001 genes differentially regulated by SN25, but not changed by ABU. FIG. 1H Moreover, host gene expression of the innate immune response genes was also activated more efficiently by SN25 than *E. coli* 83972. The expression of cytokines and cytokine receptors was enhanced in SN25-infected compared to ABU-infected human kidney cells. More highly regulated cytokines include CXCL1, 2, 3 and 8, CCL5 and 10, IL1B as well as CSF2, LTB and WNT5A. The results identify SN25 as a loss of Pol II inhibition mutant, with stronger pro-inflammatory effects than the parent strain, consistent with the loss of Pol II inhibition.

FIG. 2B List of specific mutations found. FIG. 2C List of genes mutated in SN25 and their corresponding functions.

FIG. 3A Cells were infected in suspension, stained for Pol II-Ser2 with fluorescently labeled AB and analyzed with flow cytometry. FIG. 3B Mean value of Pol II phosphorylation in control, ABU infected sample and samples infected with single gene ABU mutants as measured by flow cytometry and FIG. 3C by microscopy. It is shown that upon infection with some single gene ABU mutants, host Pol II phosphorylation becomes higher compared to ABU infection implying that these genes are involved in repression of host Pol II phosphorylation. Statistical difference in level of Pol II phosphorylation was measured with T test; FIG. 3D-E Experimental design aimed to identify the Pol II inhibitor; Bacteria taken from agar plates and suspended in PBS did not show inhibitory activity; RPMI incubated with $10^9$ CFU/mL of bacteria for 4 hours was collected, centrifuged to remove bacterial cells and filtered through a 0.2 μm filter. The filtrate contained significant inhibitory activity ($p<0.001$), suggesting that bacterial growth in cell culture medium (RPMI) induces the secretion of inhibitor(s). Screening of supernatant of mutants revealed that all single gene mutants, apart from lldD, lldR, nlpD and rfaH, secrete the substance with inhibitory activity.

FIG. 4A Eukaryotic phosphorylation machinery consists of two cyclin-dependent kinases CDK9 and 12, that phosphorylate CTD of Pol II biggest subunit at Ser2 residue. PAF complex of proteins recruits CDK12 to promoter. FIG. 4B Western blot of whole cell lysates after infection with ABU and SN25 showing decrease of expression of proteins required for Pol II phosphorylation. Table inset shows % inhibition of protein as mean value of 2 experiments. FIG. 4C Confocal microscopy of cells infected with ABU strain and SN25 reisolate. Cells were treated with anti-PAF1c or anti-CDK12 primary antibody and corresponding fluorescently labeled secondary antibodies. Nuclei were counterstained with Draq5. FIG. 4D Fluorescence intensity of staining in C was quantified by ImageJ software 1.46r. Mean values of two experiments are shown.

FIG. 4E To identify genes involved in PAF1c and CDK12 inhibition, cells were infected with single gene ABU mutants and level of PAF1C and CDK12 proteins was assessed with western blot. Table below specifies % of inhibition. NlpD was identified as gene that is primarily involved in suppression. FIG. 4F Confirmation with confocal microscopy of the effect of attenuated PAF1C and CDK12 suppression by d NlpD mutant.

FIG. 5A NlpD gene is located upstream of rpoS, which encodes Sigma S; the DNA binding subunit of bacterial RNA Polymerase. NlpD regulates Sigma S expression through internal promoter. FIG. 5B An rpoS deletion mutant was constructed in *E. coli* 83972. The loss of Sigma S protein is demonstrated by Western blot analysis of bacterial lysates of strains SN25, d nlpD and d rpoS. FIG. 5C The rpoS deletion mutant was used to infect human kidney cells. Confocal microscopy shows the reduction in Pol II Ser2, Paf1c and CDK12 levels was attenuated compared to the ABU strain. FIG. 5D Quantification of data in FIG. 5C. FIG. 5E Comparison of bacterial and eukaryotic type II RNA polymerase. Homologous subunits are similarly shaded. FIG. 5F A schematic illustration of the hypothesis for Sigma S binding to eukaryotic promoter DNA and competitive inhibition of TBP binding. FIG. 5G Testing of hypothesis in E. Human and bacterial TATA box oligonucleotides were incubated with synthetic peptide covering the DNA-binding domain of Sigma S. Sigma S is shown to bind prokaryotic and human TATA box oligonucleotides, creating band shifts with similar mobility. Specificity was confirmed by inhibition of binding with Sigma S-specific antibodies. FIG. 5H Adding of TBP with whole cell lysate to IRF3 promoter DNA leads to TBP-DNA complex. Sigma S competes with TBP for binding to IRF3 promoter as visualized by concentration dependent decrease in intensity of shifted band.

FIG. 6A Confocal imaging of infected human kidney cells after staining with antibodies specific for Pol II Ser2 and Sigma S. A parallel loss of nuclear Pol II staining and accumulation of RpoS in nuclear aggregates was detected. FIG. 6B Detection by Western blots of Sigma S in whole cell extracts and the nuclear fraction of cells infected with the ABU strain. Sigma S was not detected in cells infected with the SN25 reisolate or nlpD or rpoS deletion mutants. FIG. 6C Binding of Sigma S and NlpD to the Pol II complex is illustrated and detected by western blot after co-immunoprecipitation of whole cell lysates with antibodies specific for total Pol II. FIG. 6D Confocal imaging of human kidney cells, infected with E. coli 83972WT and stained with antibodies specific for Sigma S or Pol II, with nuclear DRAQ5 counterstaining.

FIG. 7A Asymptomatic bacteriuria in C57BL/6 WT mice. Mice were inoculated with 2×10$^5$ CFU/mL of ABU 83972, SN25, delta-nlpD or delta-rpoS. Mice were sacrificed after 24 hours and bladder tissues were stained with a-Pol IIp Ab. FIG. 7B Loss Pol II phosphorylation is apparent after infection with ABU, this is rescued after infection with SN25, d nlpD and d rpoS mutants. This confirms in vitro data on NlpD and RpoS being involved in inhibition of Pol II phosphorylation. FIG. 7C Neutrophil counts of urine of mice infected with ABU, SN25, d nlpD and d rpoS mutants. Functional relevance of Pol II de-repression in SN25 infected mutant is further suggested by higher neutrophil counts.

EXAMPLE 1

Inhibition of Eukaryotic RNA Pol II Phosphorylation by 83972 ABU Strain

Figure 1A:
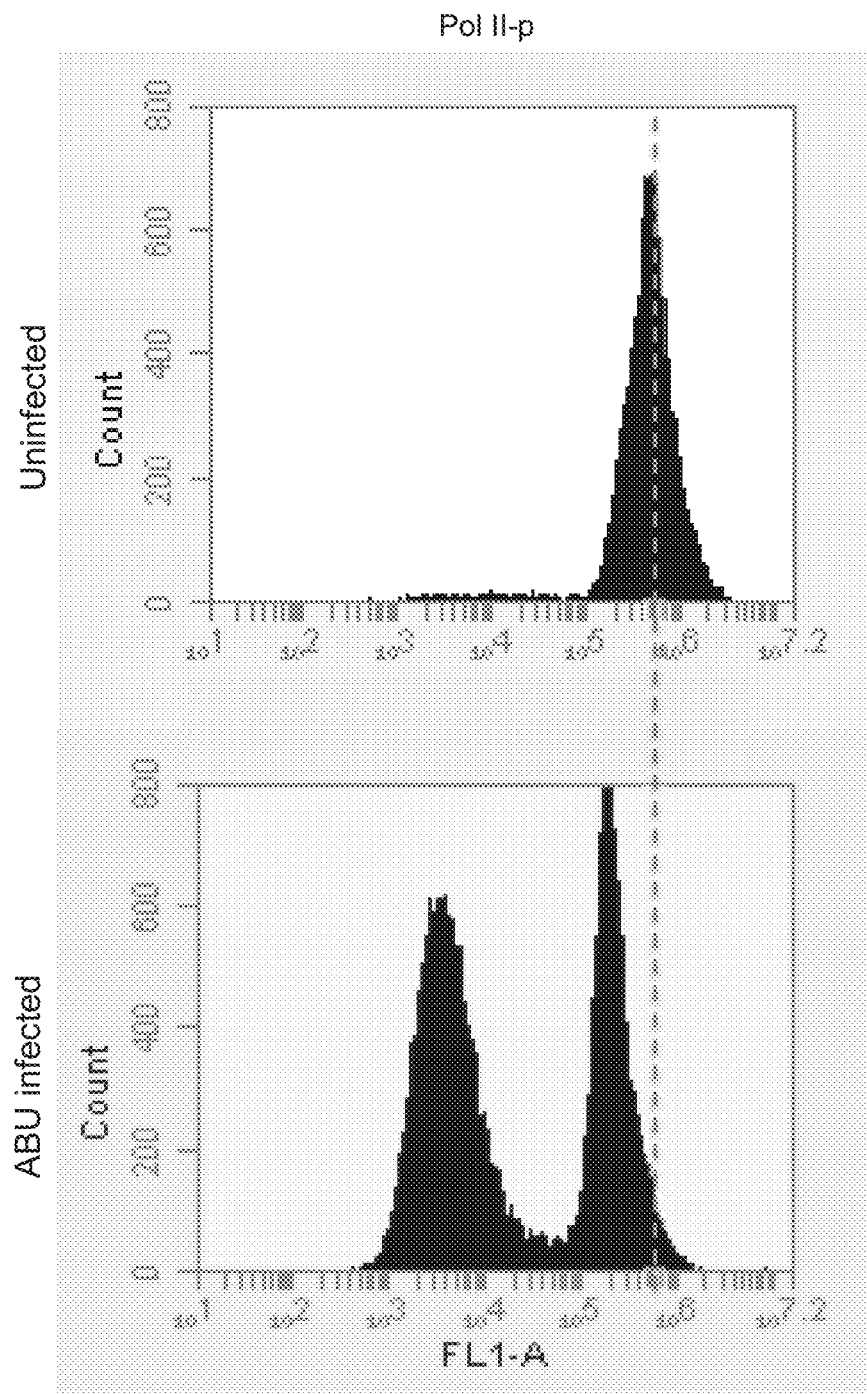
FIG. 1A-H illustrates inhibition of eukaryotic RNA Pol II phosphorylation by 83972 ABU strain.

The productive mRNA elongation step is generally marked by the phosphorylation of Pol II carboxy terminal domain on Serine-2 residues, consequently, Ser2 phosphorylation of Pol II is a good indicator of its activation. As a starting point, flow cytometry was developed as a technology to quantify Pol II phosphorylation (FIG. 1). Human kidney epithelial A498 cells were infected with ABU 83972 strain for 4 hours and after fixing and permeabilization, cells were stained with antibodies against phosphorylated Ser-2 in Pol II and goat anti-rabbit secondary antibodies labelled with Alexa-fluor 488. A marked reduction in Ser 2 phosphorylation was detected, compared to uninfected cells (FIG. 1A).

Figure 1B:
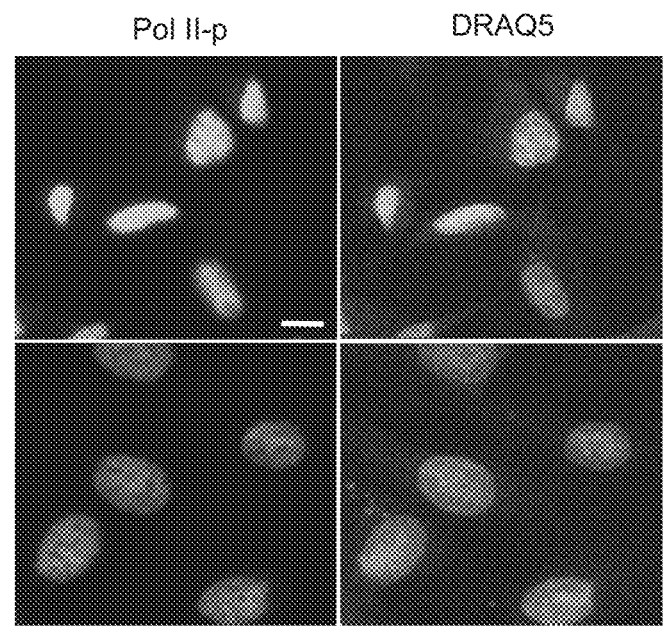
Figure 1C:
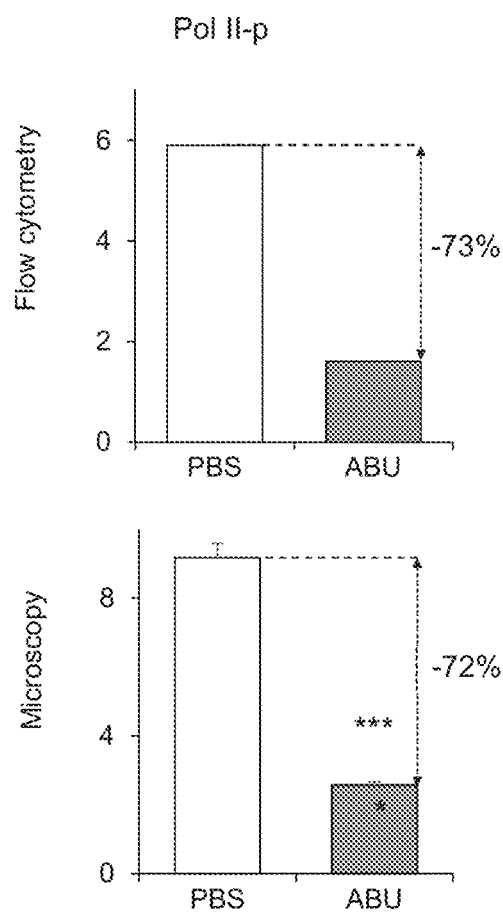

This effect was also confirmed using confocal microscopy (FIG. 1B). Infection with E. coli 83972 induced a change in the magnitude and distribution of phosphorylation, compared to uninfected cells. The loss of Pol II staining was visible as a loss in total fluorescence (mean value of 158, 493 AU compared to 588,307 AU, p<0.001), (FIG. 1C). In addition, a change in distribution resulted in the emergence of two peaks, with intensities of 5,522 and 256,779 AU. Uninfected cells showed one single peak with higher fluorescence intensity at 605,108 AU. Pol II inhibition was also clearly visible using confocal microscopy (FIG. 1B). The results confirm the inhibition of eukaryotic RNA Pol II phosphorylation by E. coli 83972.

To refine the Pol II phosphorylation data for middle-size events, Pol II phosphorylation was measured for events within gate R2. A higher number of cells fell into gate R2 for control compared to ABU infected sample (76.2 and 35.2%). ABU infection causes formation of smaller cells or broken cells (nuclei) when compared to uninfected sample as was seen from the number of small-size events. When R2-gated events are taken into consideration, lower-intensity peak of Pol II fluorescence in ABU sample becomes much less prominent. Mean value of Pol II phosphorylation in control and ABU infected sample for the representative experiment was 510,668 and 222, 972 AU, respectively.

EXAMPLE 2

Identification of an ABU 83972 Variant SN25 with Loss of Pol II Inhibitory Activity and its Genome Sequencing Patients were inoculated with therapeutic doses of ABU 83972. The protocol for therapeutic bladder inoculation of patients with E. coli 83972 has been described previously (Agace, J Clin Invest, 1993; Wullt, Mol Microbiol, 2000; Sundén, J Urol, 2010). Briefly, after antibiotic treatment to remove prior infection, patients were inoculated with E. coli 83972 through a catheter (30 ml, 10$^5$ cfu/ml in saline). Blood and urine samples were obtained before and repeatedly after inoculation. Throughout the colonization period, viable bacterial counts in urine were determined, monthly urine samples were collected and analyzed for IL-6 and IL-8 as well as neutrophil infiltration. Bacteria from each urine sample were verified by PCR for presence of a kryptic plasmid unique for strain 83972 and one chromosomal marker (4.7-kb deletion in strain 83972 in the type 1 fimbrial gene cluster). For further analysis, five independent colonies per urine sample were used.

Figure 1D:
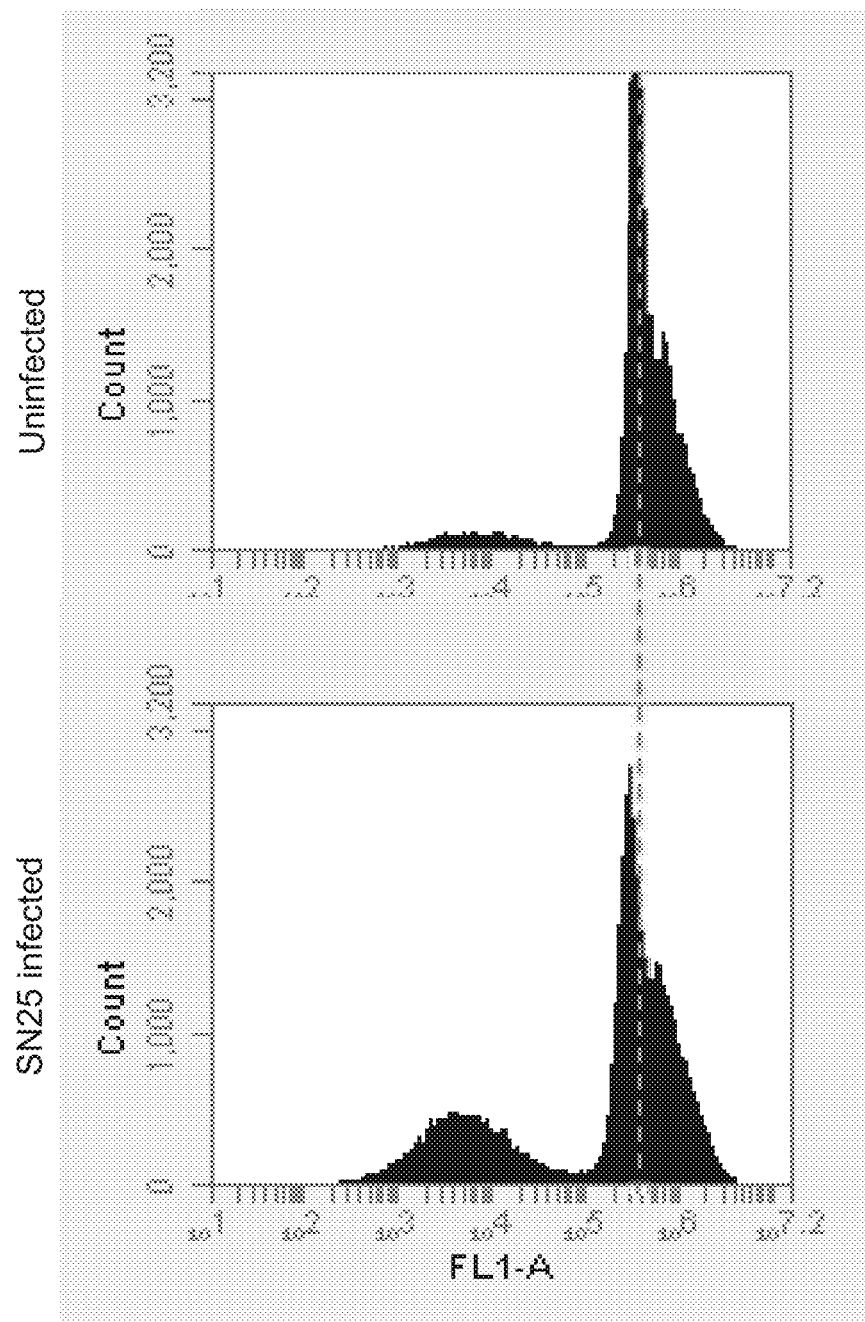
Figure 1E:
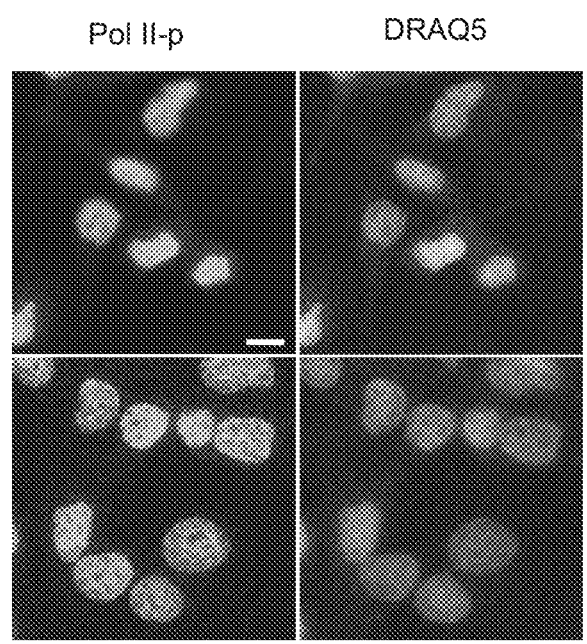
Figure 1F:
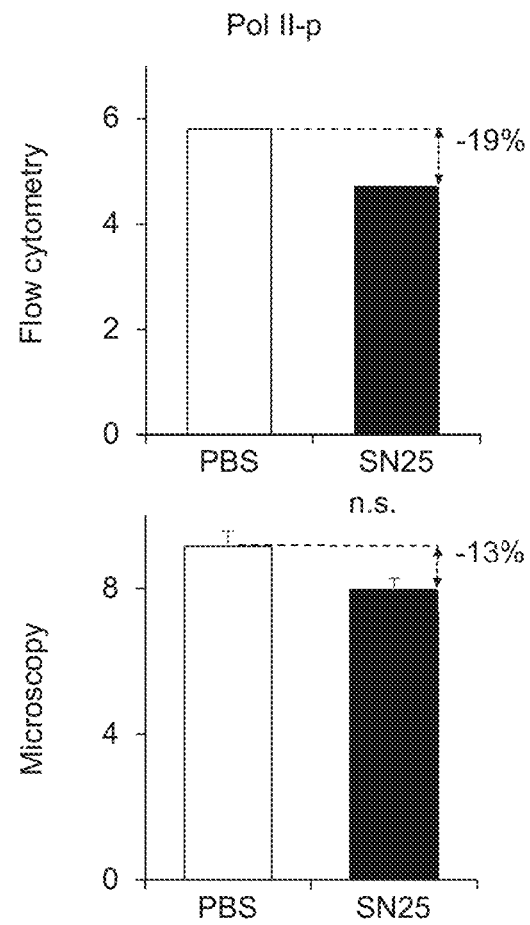
Figure 1G:
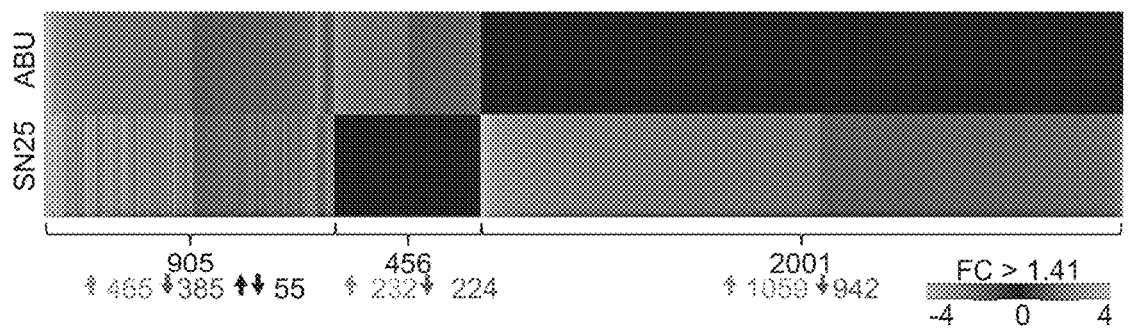
Figure 1H:
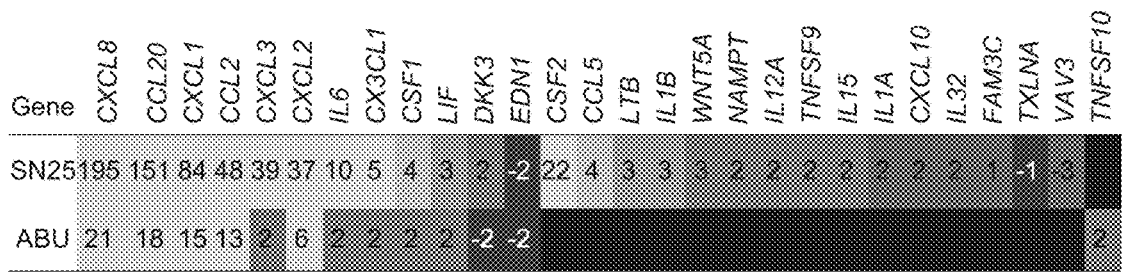

Re-isolates from inoculated patients were then screened for Pol II inhibitory activity as described in Example 1. One re-isolate, designated SN25, had lost Pol II inhibitory activity (FIG. 1D). A498 cells were infected with ABU or SN25 E. coli strain and labelled for phosphorylated Pol II as described above. Mean values of RNA Pol II phosphorylation in SN25-infected samples compared to uninfected control cells and obtained with flow cytometry and confocal microscopy, are shown in (FIGS. 1E and 1F, respectively). The ABU strain suppressed Pol II phosphorylation by about 73%, while SN25 by only 19%, suggesting that some genes in SN25 genome, responsible for suppression of Pol II phosphorylation, might have been lost or inactivated.

Figure 2A:
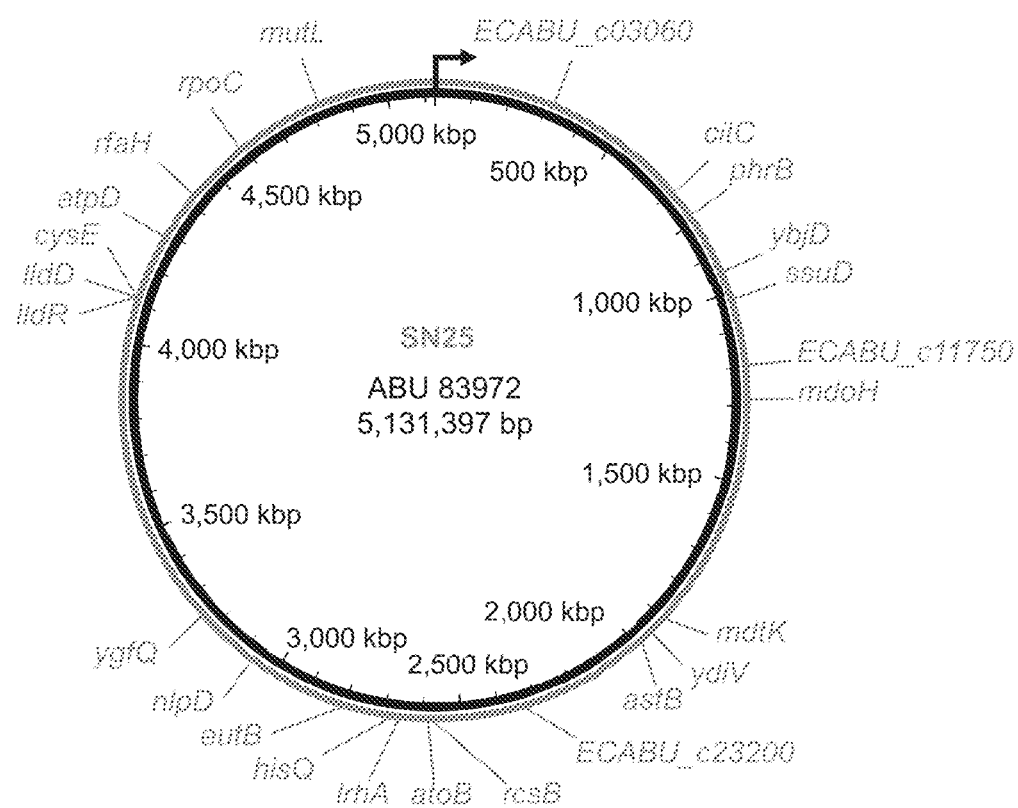
FIG. 2A Schematic location of mutations in SN25 genome compared to ABU 83972.

Genome of SN25 was sequenced (FIG. 2A) to identify responsible mutations, and 36 genomic changes were found compared to E. coli 83972 wt; 25 of them were in coding region with 8 resulting in amino acid change (FIG. 2B). Among the affected genes are those, responsible for L-lactate metabolism (lldD and lldR), regulation of motility and chemotaxis (lrhA), cell wall formation (nlpD) and biofilm formation (rfaH and cysE) (FIG. 2C). RfaH is a transcriptional anti-terminator, required for efficient expression of long chain LPS expression and hemolysin, its loss attenuates virulence of UPEC. CysE is a serine acetyltransferase, catalyzes the conversion of L-serine to O-acetyl-L-serine. Inactivation of mdoH leads to increased expression of colanic acid capsular polysaccharide. RcsB is a positive response regulator for colanic capsule biosynthesis.

EXAMPLE 3

Figure 3A:
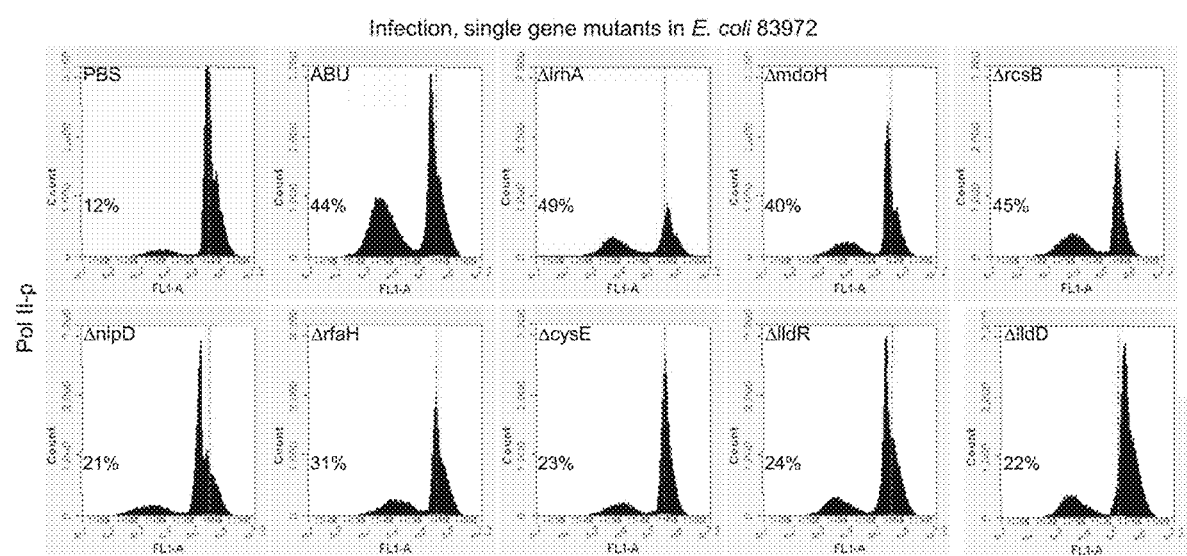
FIG. 3A-E illustrates the effect on Pol II phosphorylation of ABU deletion mutant reproducing the genomic changes in SN25. The following genes were deleted from 83972 ABU genome: lldD, lldR, nlpD, rfaH, cysE, rcsB, mdoH and lrhA. These mutants were studied with flow cytometry and fluorescence scanning microscopy for level of Pol II phosphorylation.
Figure 3B:
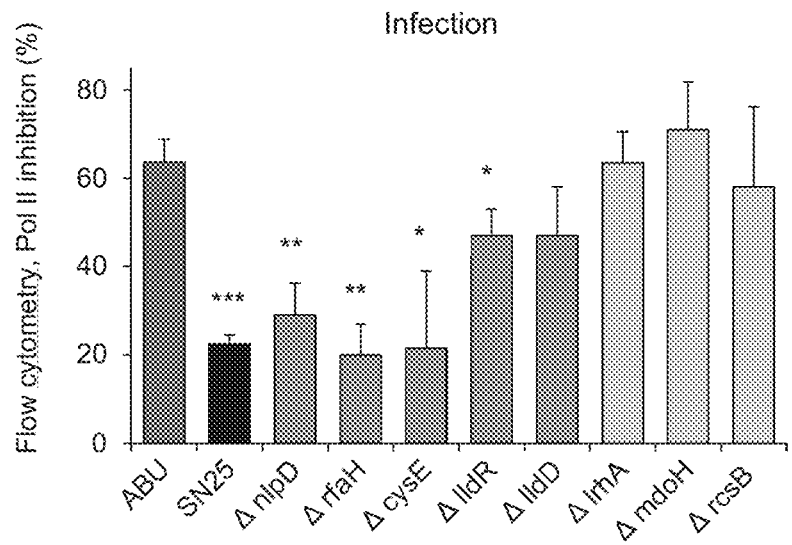
Figure 3C:
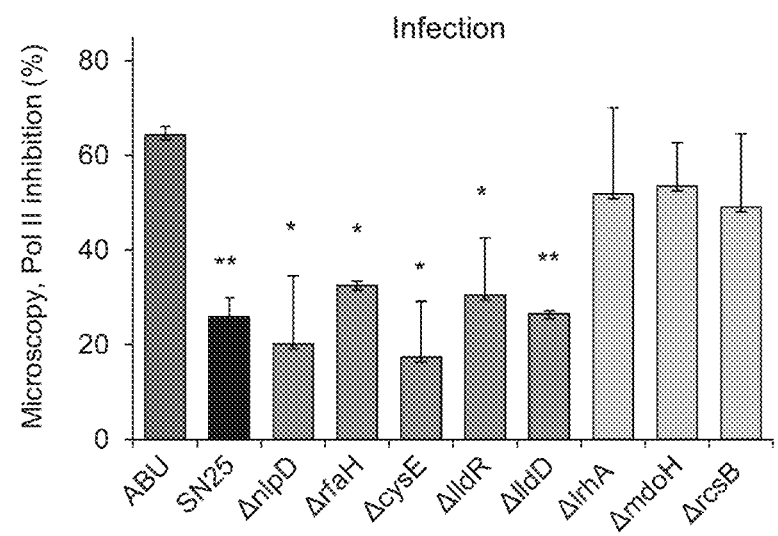
Figure 3E:
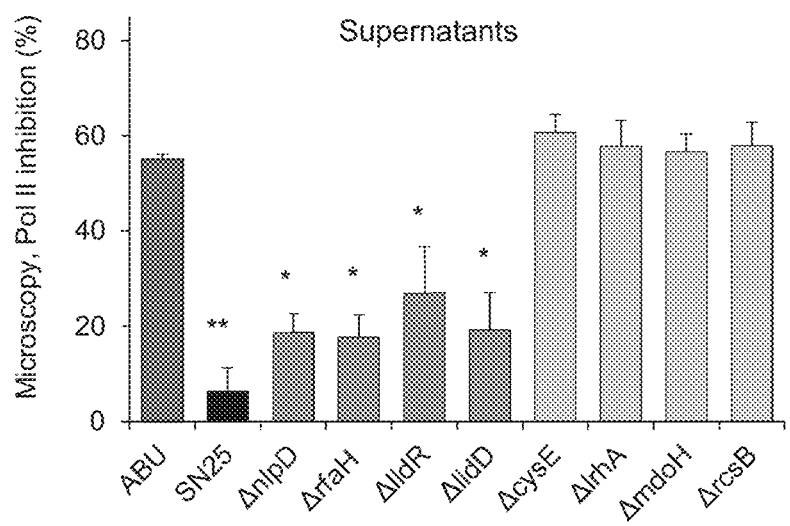
Figure 3D:
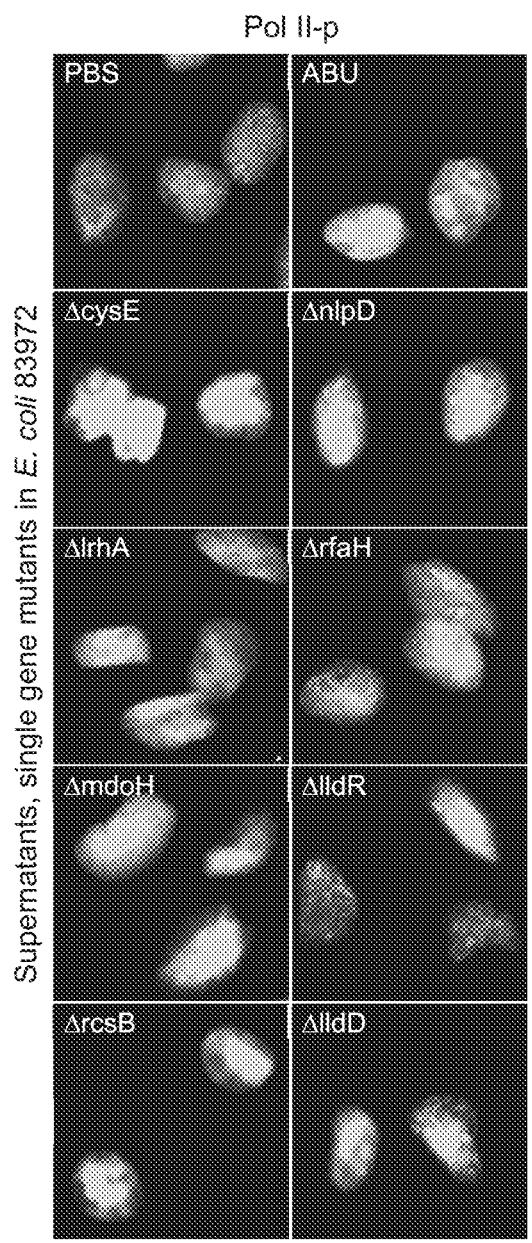

Screening of Single-Gene Mutants to Identify Genes Responsible for Pol II Inhibition To identify genetic determinants of Pol II phosphorylation, genes comprising the identified variant sequences were replaced in E. coli 83972 chromosome by homologous recombination with chloramphenicol resistance cassette. Deletions were validated (Uli). The mutants were subsequently screened for effects on Pol II (FIG. 3A). Single deletions of ΔlldD, ΔlldR, ΔnlpD, ΔrfaH and ΔcysE reduced the inhibitory effect of E. coli 83972 wt, as shown by flow cytometry and confocal microscopy (FIG. 3B-C). Statistical difference in level of Pol II phosphorylation was measured with t test.

The lldD gene is responsible for aerobic L-lactate metabolism, whose product catalyzes the interconversion of L-lactate and pyruvate, while lldR is a regulator of the lldPRD operon. It was concluded from these data that products of both lldD and lldR genes are responsible for suppression of RNA Polymerase II phosphorylation. The low-intensity Pol II phosphorylation peak is less prominent after infection with SN25, ABU ΔlldD and ABU ΔlldR, which is in agreement with higher mean values of Pol II phosphorylation for cells infected with SN25 and ABU mutants compared to ABU. As shown, mean Pol II phosphorylation for ungated events for control cells and cells infected with ABU, SN25, ABU ΔlldD and ABU ΔlldR is 100, 78, 79, 50 and 50%, respectively. Thus, the products of lldD ($p<0.4$) and lldR genes lead to inhibition of Pol II phosphorylation, with effect of lldR being statistically significant ($p<0.05$).

Several other mutants, which had significant effect on de-repression of Pol II phosphorylation, are 83972ΔnlpD ($p<0.01$), 83972ΔrfaH ($p<0.01$) and 83972ΔcysE ($p<0.05$) (FIGS. 3 B and C). Gene nlpD encodes a lipoprotein with a potential function in cell wall formation. Gene rfaH encodes for a transcriptional anti-terminator, required for efficient expression of long chain LPS, hemolysin and affects biofilm formation. Gene cysE encodes for serine acetyltransferase, which catalyzes the conversion of L-serine to O-acetyl-L-serine that is the first step of L-cysteine biosynthesis from L-serine; cysE product also affects biofilm formation in *E. coli* K-12.

EXAMPLE 4

Secretion of Bacterial Inhibitors of Pol II Phosphorylation

In parallel with the genetic studies, a biochemical approach was taken to identify the compound responsible for the Pol II inhibitory activity. Bacteria were incubated for 4 hours in tissue culture medium (RPMI supplemented with 1 mM pyruvate). The medium was harvested after 4 hours, centrifuged at 4,000×g for 10 min and sterile filtered to remove remaining bacteria (0.2 μm filter), before addition to human kidney cells (FIG. 3D). *E. coli* are typically 2 μm long and 0.5 μm in diameter, and filtration through 0.2 μm syringe filters removes bacterial cells. Significant Pol II inhibitory activity ($p=0.023$) was identified in the ABU culture supernatants compared to uninfected, substituted RPMI, suggesting that growth in cell-free culture medium induced the secretion of the inhibitor(s).

As it was shown that supernatant of ABU bacteria have similar inhibitory effect on Pol II as ABU bacteria per se, we questioned if this effect is lost in the SN25 supernatant. Phosphorylation of Pol II was significantly higher ($p<0.05$) after incubation with SN25 supernatant compared to ABU supernatant, suggesting that the strain has lost the ability secrete inhibitors. Mutants of SN25 were therefore were grown in RPMI and their supernatants were harvested. Supernatants of lldD, lldR, nlpD and rfaH mutants had lost Pol II inhibitory activity ($p<0.02$ and $p<0.05$, respectively) compared to ABU supernatant, (FIG. 3E) indicating that genes lldD, lldR and nldD achieve their effect via effector molecules that are secreted by the bacteria.

The inhibitory activity of the supernatant was shown to be heat sensitive (100° C., 30 min) but Proteinase K resistant. The molecular size of the inhibitory component was found to be <3 kDa, by centrifugal ultrafiltration with a 3 kDa filter. Elevated levels of acetic acid and formic acid were detected in the filtrate of the ABU supernatant, using ion exchange chromatography. A rapid increase in formic-, succinic- and acetic acids was also detected by Mass spectrometry analysis of metabolites secreted by ABU upon growth in urine. Finally, high concentrations of formic and acetic acids were shown to inhibit Pol II phosphorylation ($\chi^2$ test for independence compared to medium control).

EXAMPLE 5

Figure 4A:
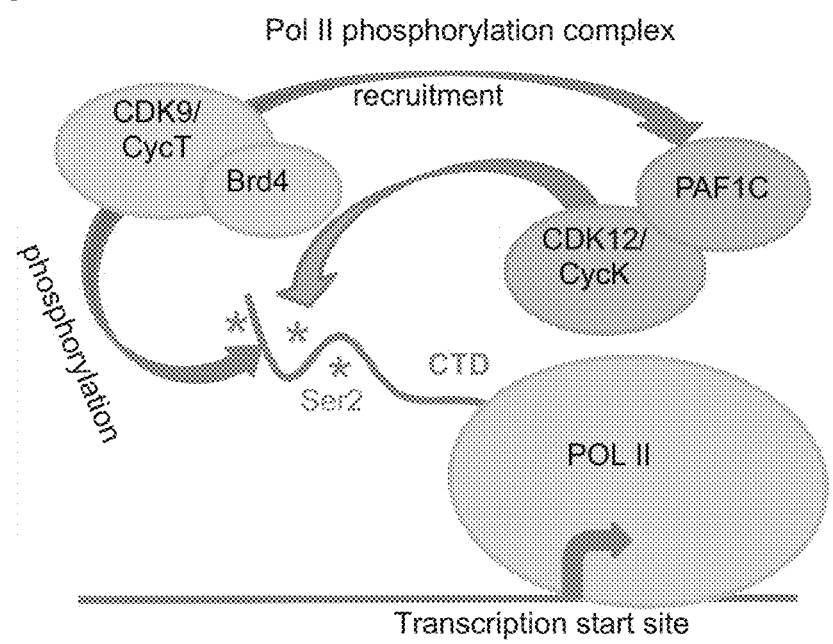
FIG. 4A-F illustrates how the ABU strain inhibits the Pol II Ser2 CTD phosphorylating machinery by targeting cyclin kinase 12 and its recruiting protein PAF1C.

The ABU strain inhibits the Pol II Ser2 CTD phosphorylating machinery by targeting cyclin kinase 12 and its recruiting protein PAF1C The Pol II phosphorylation complex required to phosphorylate Ser2 is assembled in several steps (FIG. 4A). The preinitiation complex containing the TATA box binding protein (TBP), binds to DNA upstream of the transcription start site and the activated complex then recruits transcription factor IID, and the N-terminal Zink ribbon domain of TFII b is required to recruit Pol II. following the binding of TATA box binding to DNA, TBP recruits Pol II and the DNA-binding. The DNA binding subunit of Pol II anchors the preformed complex to DNA recruits Pol II to different eukaryotic promoters and the beta subunit is phosphorylated by the C-terminal domain (CTD) phosphorylation machinery. Cyclin-dependent kinase 9 (CDK9) brings the adaptor PAF1C into close proximity with Pol II and the PAF1C subunit CDC73 recruits CDK12 to the complex. CDK9 and CDK12 then phosphorylate the Pol II CTD domain, at Ser 2 (FIG. 4A).

To examine how the ABU strain suppresses phosphorylation of host RNA polymerase II CTD at Ser2 residue (FIG. 5E), we further analyzed potential protein targets in the Pol II phosphorylation pathway. Two cyclin dependent kinases are responsible for Pol II phosphorylation, —CDK9 and CDK12 (FIG. 4a). CDK9 is involved as well, bringing PAF1C in close proximity to the Pol II promoter complex. PAF1C acts as a recruitment protein for CDK12.

Figure 4B:
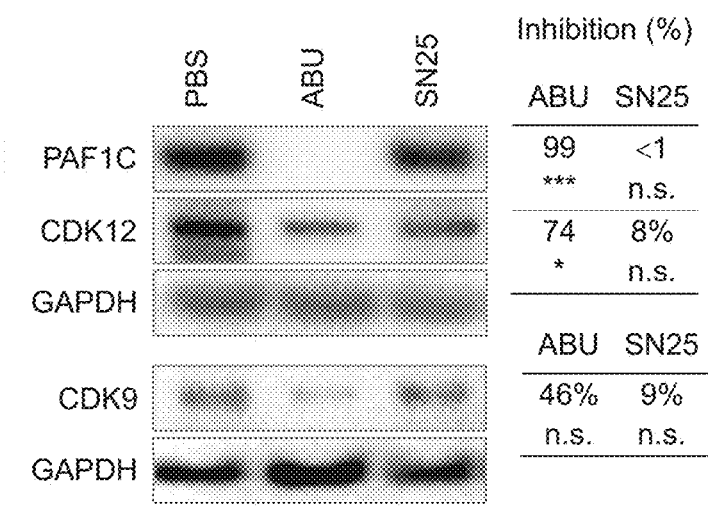
Figure 4C:
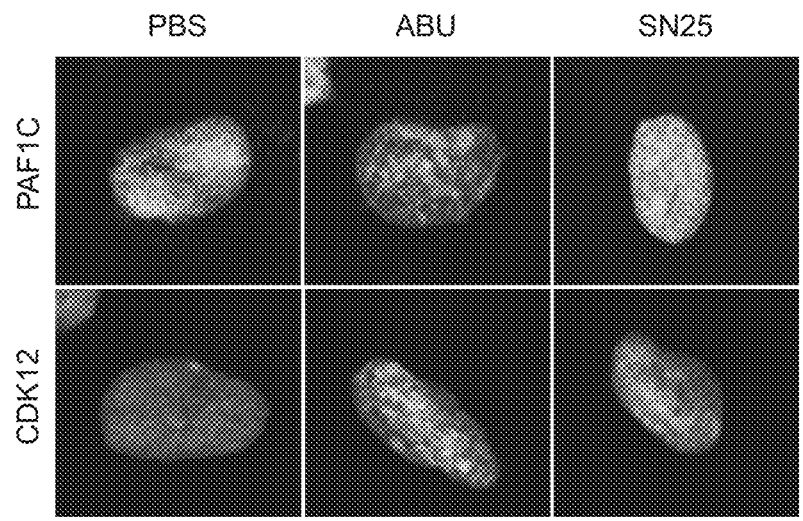
Figure 4D:
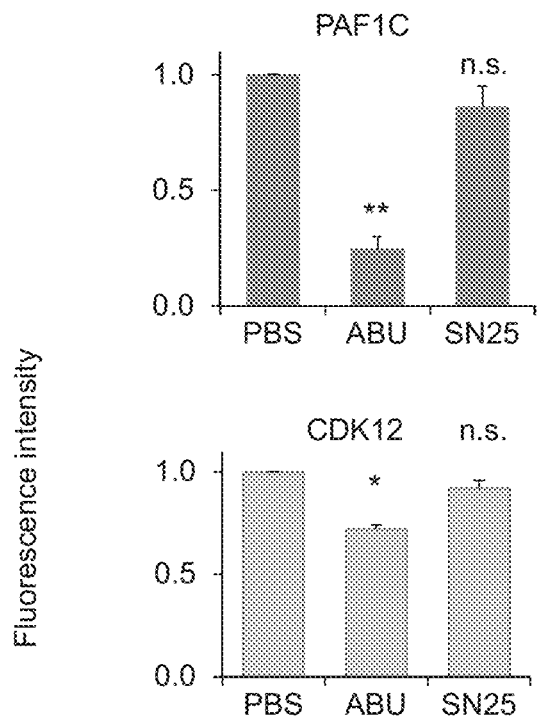

To address how *E. coli* 83972 inhibits the Pol II phosphorylation machinery, CDK12, CDC73 (PAF1C subunit) and CDK9 in host cells, after infection with ABU and SN25 was quantified by Western Blot analysis (FIG. 4B). CDK12 and PAF1 decreased drastically after ABU infection but remained at control levels after SN25 infection. CDK9 levels were less strongly affected (40%). This effect on PAF1C and CDK12 was confirmed by confocal microscopy (FIG. 4C-D). SN25, in contrast, did not significantly alter PAF1C, CDK12 or CDK9 protein levels compared to uninfected cells.

Figure 4E:
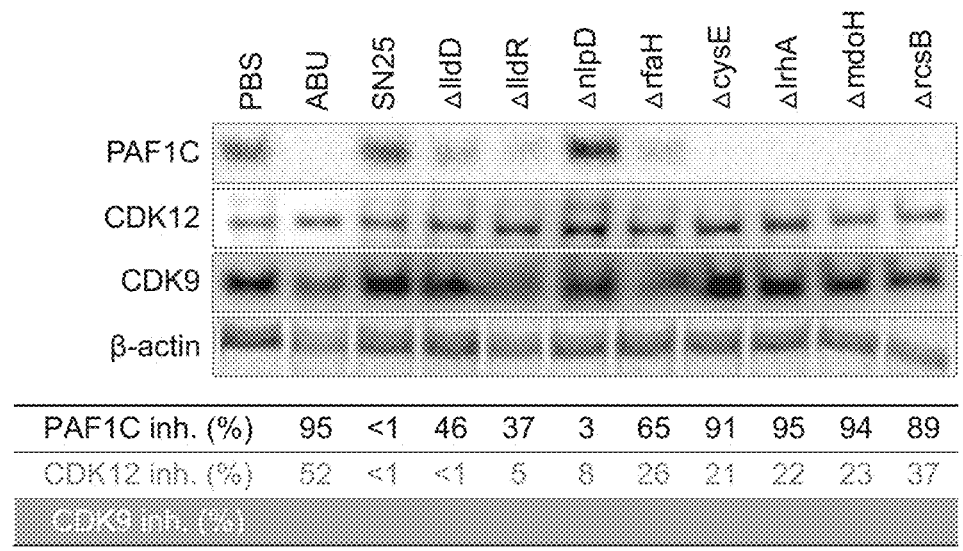
Figure 4F:
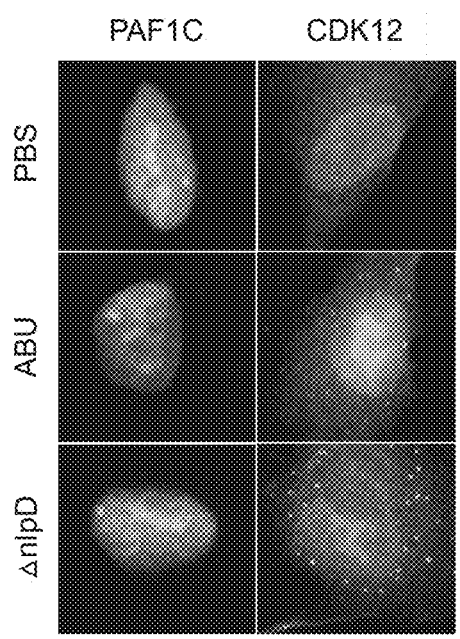
Figure 5A:
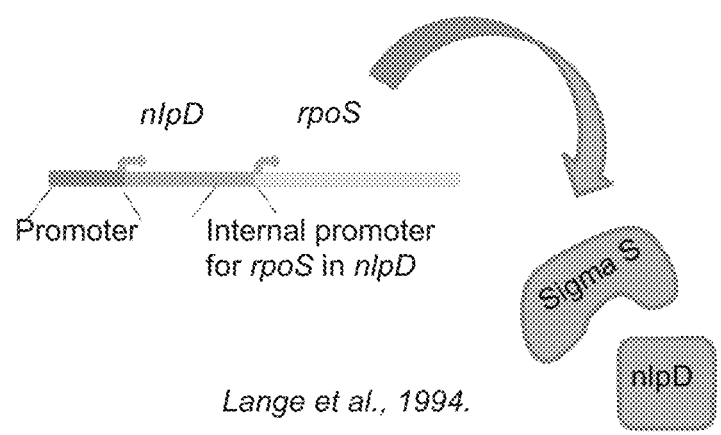
FIG. 5A-H. Sigma S as an effector molecule suppressing host gene expression.

To address if the inhibitory activity was a secreted bacterial product, A498 cells were treated with supernatants of cells infected with the single gene mutants of the ABU strain, and CDK12 and CDC73 levels were subsequently tested in WB. The results are shown in FIG. 4E. The nlpD deletion mutant had lost the inhibitory activity against PAF1 and CDK12. This was confirmed by confocal microscopy (FIG. 4F). NlpD gene is located in one gene cluster with rpoS, encoding one of sigma subunits of bacterial RNA polymerase (FIG. 5A). Remarkably, the list of genes related to CDK12 and CDC73 suppression showed a direct association with the list of genes with effect on Pol II phosphorylation. In contrast, nlpD, lldD, lldR and rfaH mutations did not affect CDK12 or CDC73 and the cysE, lrhA, mdoH and rcsB deletion mutants resembled SN25.

Overall, these results indicate that nlpD and rpoS suppress Pol II phosphorylation by targeting the CDK12 and PAF1C arm of host phosphorylating machinery.

EXAMPLE 6

Investigation into NlpD and RpoS

Figure 5B:
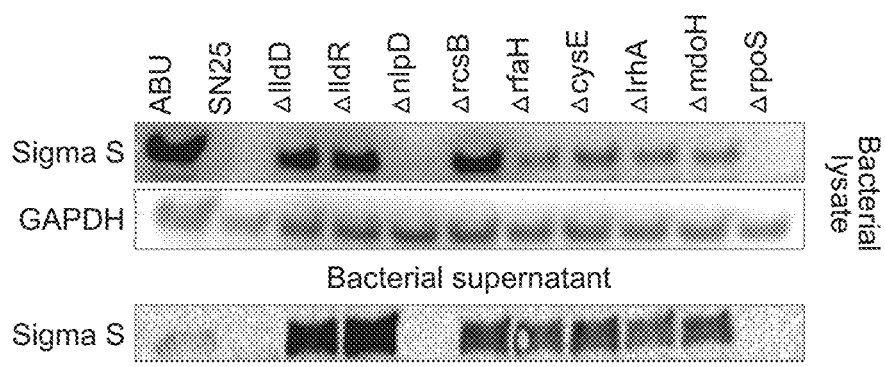

In *E. coli* 83972, NlpD is located upstream of rpoS, which encodes Sigma S; the DNA binding subunit of bacterial RNA Polymerase (FIG. 5A). NlpD regulates Sigma S expression and may facilitate its release by activating cell wall hydrolases. To address if the effects of NlpD on Pol II and PAF are executed through rpoS, we constructed an rpoS deletion mutant in *E. coli* 83972. The deletion was confirmed by DNA sequencing and the loss of Sigma S protein was verified by Western blot analysis of bacterial cell extracts (FIG. 5B). Sigma S was present in extracts from *E. coli* 83972WT bacteria but was absent in extracts from SN25, ΔnlpD and ΔrpoS. In bacterial supernatants, the loss of Sigma S in these strains was confirmed (FIG. 5B).

Figure 5C:
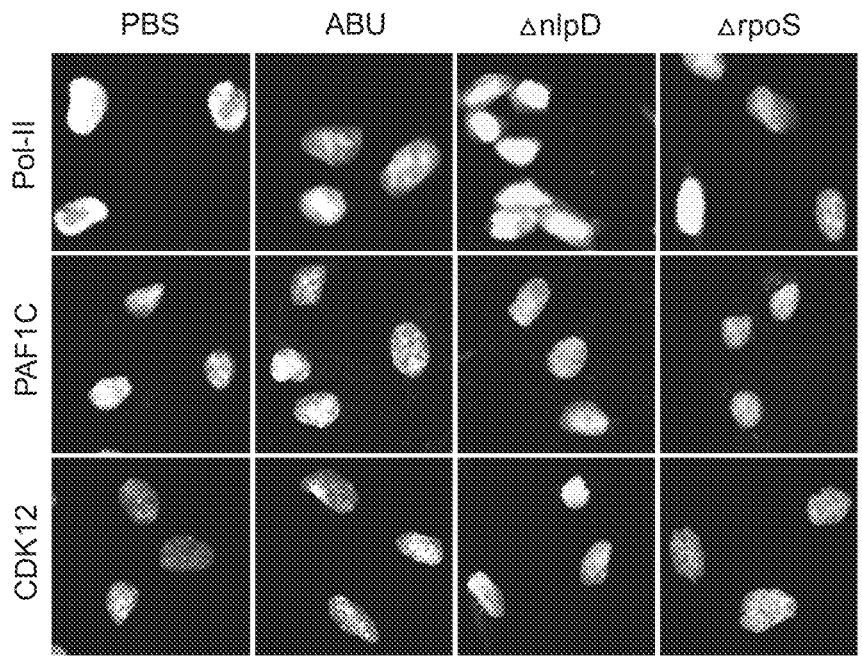
Figure 6A:
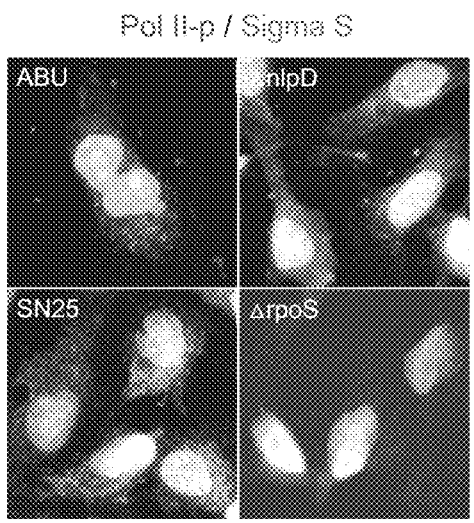
FIG. 6A-D. Interactions of Sigma S and NlpD with the Pol II complex.
Figure 6A:
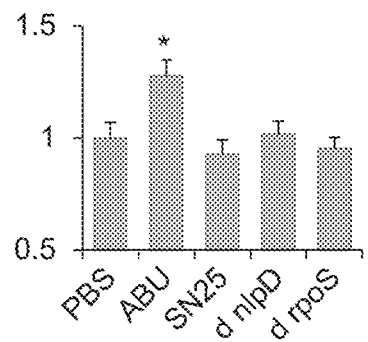
Figure 6B:
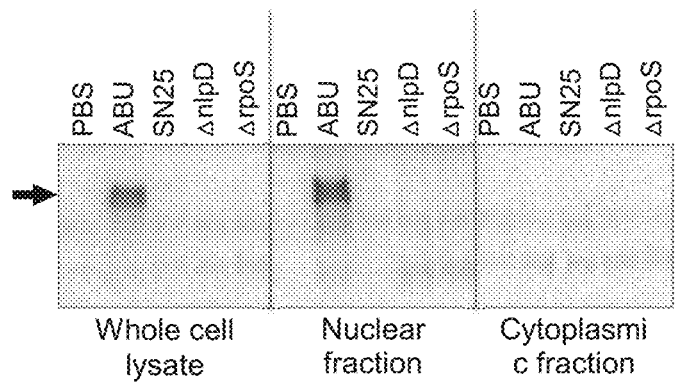
Figure 6C:
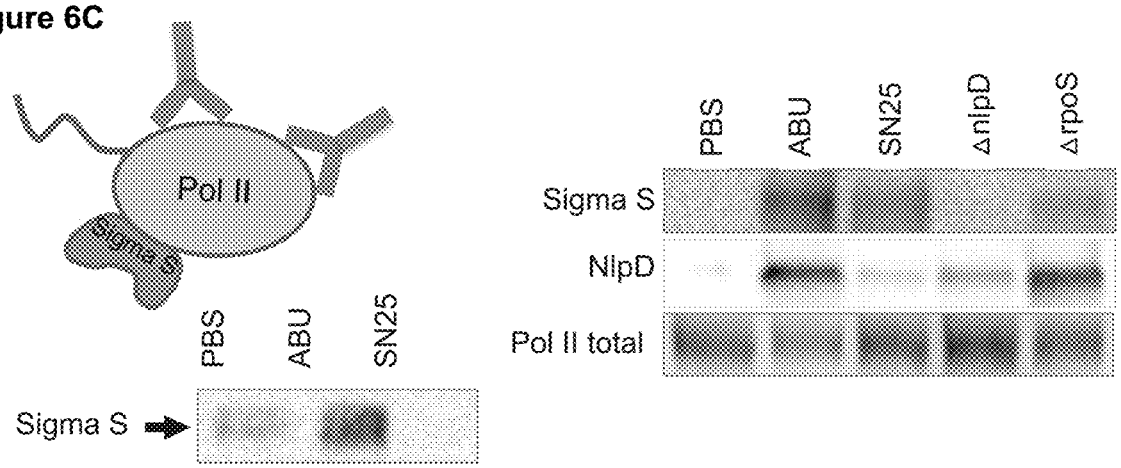
Figure 6D:
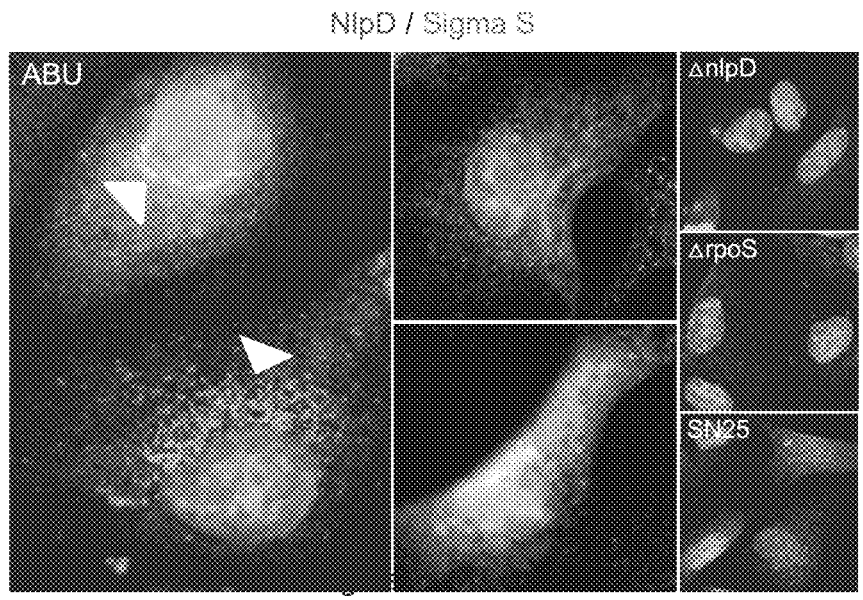

The applicants subsequently examined the effect of the rpoS mutant on Pol II phosphorylation (FIG. 5C). The rpoS mutant had lost the ability to inhibit Pol II phosphorylation, and Pol II staining in infected cells was comparable to SN25 and the delta NlpD mutant (n.s.). A similar effect was observed for PAF1C, CDK12 as the rpoS mutant had lost the ability to inhibit PAF and CDK12 (FIGS. 6C-D). The results suggest that Sigma S acts as bacterial effector molecules in human cells, responsible for the inhibition of Pol II phosphorylation through PAF1C. The results suggest that the effects of NlpD on RpoS account for the attenuation of Pol II-Ser 2 phosphorylation.

EXAMPLE 7

Subcellular Distribution of nlpD and rpoS in Infected Human Cells

To address if these molecular interactions may be relevant in infected cells, the applicants subsequently examined, if Sigma S is internalized into human cells, after infection with *E. coli* 83972WT. By Western blot analysis of whole cell extracts, a single band of 40 kDa was detected, after staining with Sigma S specific antibodies. A band with similar mobility was detected in nuclear extracts, suggesting nuclear translocation of Sigma S (FIG. 6B). The Sigma S band was not detected in cells infected with SN25 or the ΔnlpD- or ΔrpoS deletion mutants.

The internalization and nuclear translocation of Sigma S was confirmed, by co-immunoprecipitation, using Pol II specific antibodies. A band corresponding to Sigma S was detected in extracts from cells infected with ABU but not SN25. In a further Pol II co-ip involving whole cell extracts from cells infected with the NlpD or RpoS mutants, Sigma S and NLPD bands were detected in ABU infected cells but not in the single gene mutants. Low Sigma S in SN25, which does not carry a deletion.

In addition, human kidney cells were infected with *E. coli* 83972WT and stained with antibodies specific for Sigma S or Pol II, with nuclear DRAQ5 counterstaining. A parallel loss of nuclear Pol II staining and accumulation of RpoS in nuclear aggregates was detected. In contrast, Sigma S was not detected in cells infected with SN25, ΔrpoS or ΔnlpD (FIG. 6D).

EXAMPLE 8

Competitive Inhibition of TBP Binding by Sigma S

The Pol II phosphorylation complex required to phosphorylate Ser2 is assembled in several steps (FIG. 4A). The preinitiation complex containing the TATA box binding protein (TBP), binds to DNA upstream of the transcription start site and the activated complex then recruits transcription factor IID, and the N-terminal Zink ribbon domain of TFII b is required to recruit Pol II. following the binding of TATA box binding to DNA, TBP recruits Pol II.

Figure 5D:
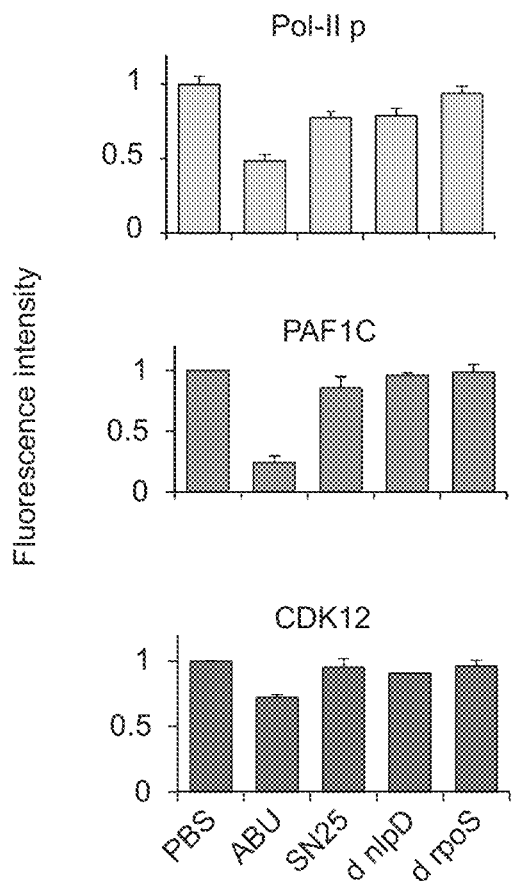
Figure 5E:
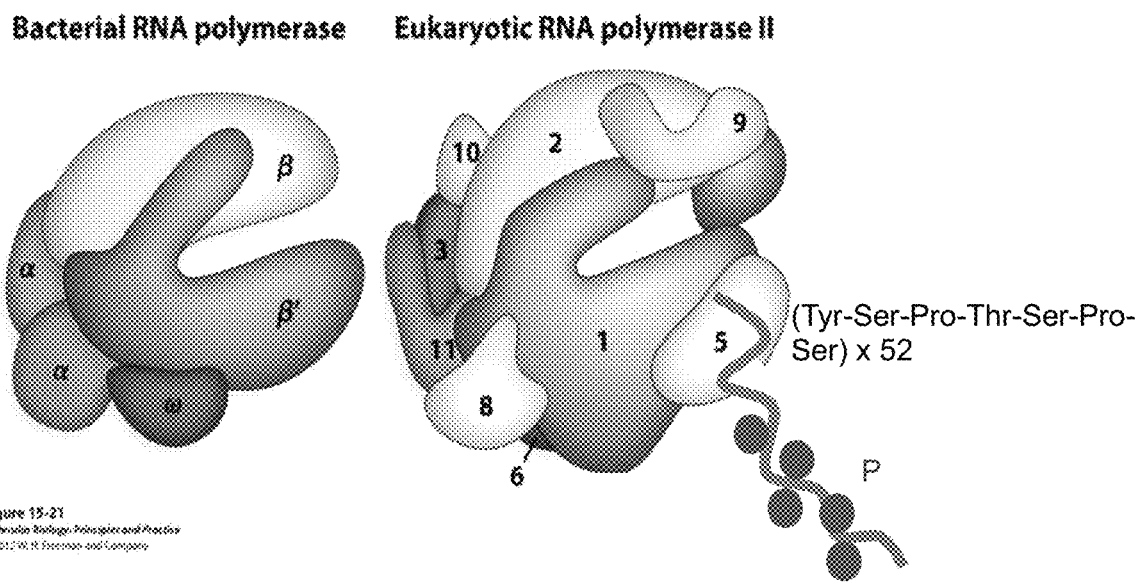
Figure 5F:
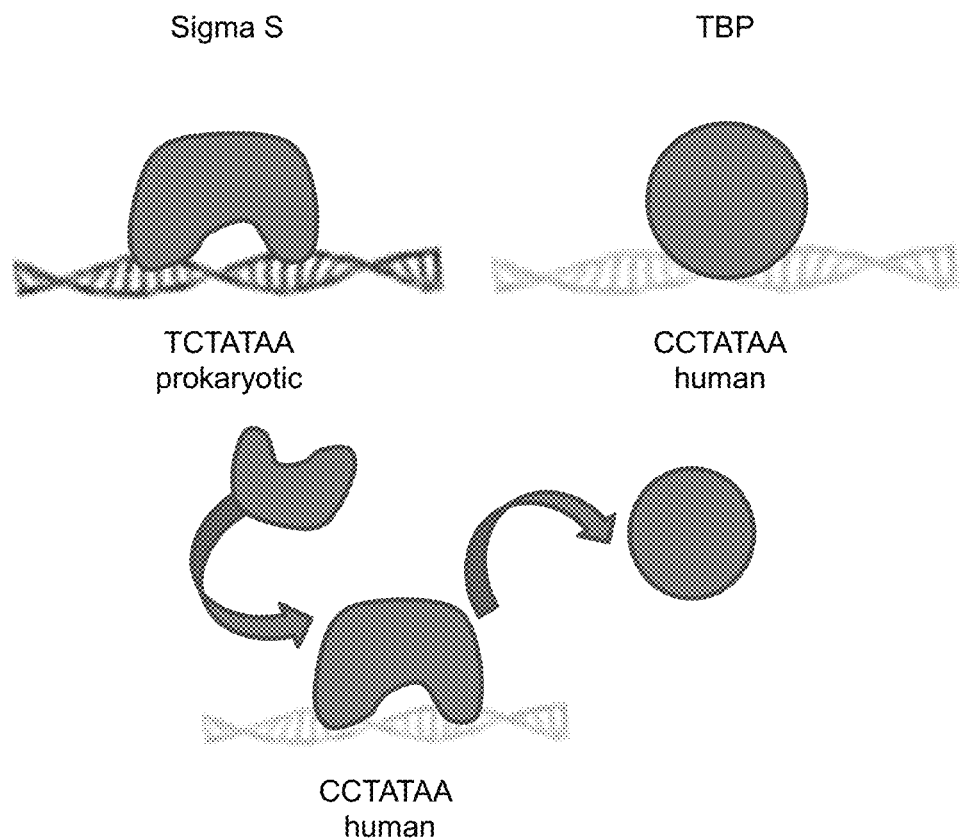
Figure 5G:
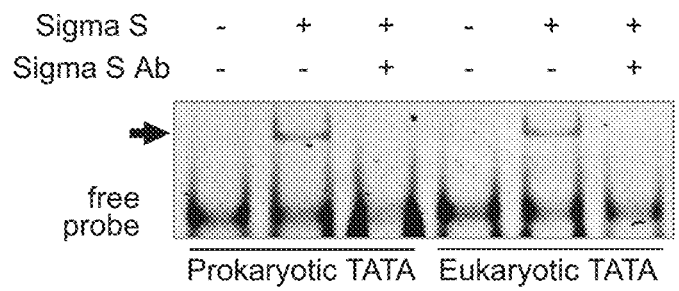
Figure 5H:
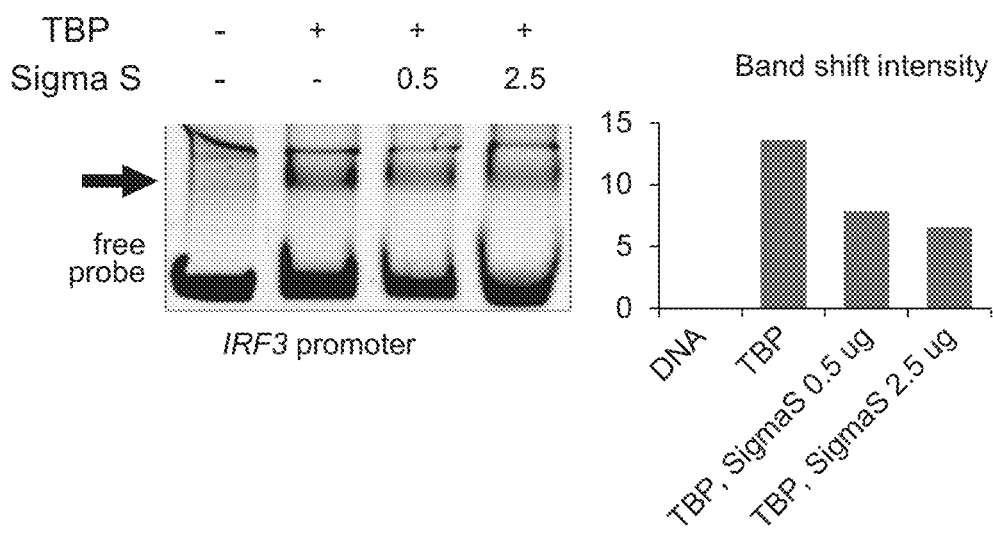

Like the TATA-box binding protein in eukaryotes, Sigma S binds to DNA and is the TATA box binding protein of the bacterial RNA Pol II complex (FIG. 5E). We therefore tested the hypothesis that Sigma S may bind to eukaryotic promoter DNA and competitively inhibit TBP binding (FIG. 5F). Human and bacterial TATA box oligonucleotides were incubated with a synthetic peptide comprising the Sigma S DNA-binding domain (aa 149-183—SEQ ID NO 2) in an electro-mobility shift assay (EMSA). Sigma S was shown to bind prokaryotic and human TATA box oligonucleotides, creating band shifts with similar mobility (FIG. 5G). Specificity was confirmed by inhibition of the band shift with Sigma S-specific antibodies. The Sigma S peptide was subsequently shown to competitively inhibit TBP binding to the IRF3 promoter, in a concentration-dependent manner (FIG. 5H).

To examine if *E. coli* 83972 affects PIC formation in infected cells, we quantified the TATA box binding protein (TBP) in total cell extracts from uninfected and infected kidney cells (FIG. 5B-D). *E. coli* 83972 reduced the TBP and TF2b protein levels. By confocal microscopy, nuclear transcription factor II b (TF2b) staining was reduced. SN25, in contrast, did not affect the PIC components (FIGS. 5C and D) and the nlpD deletion mutant reproduced the SN25 phenotype (FIG. 5F).

EXAMPLE 9

In Vivo Relevance

Figure 7A:
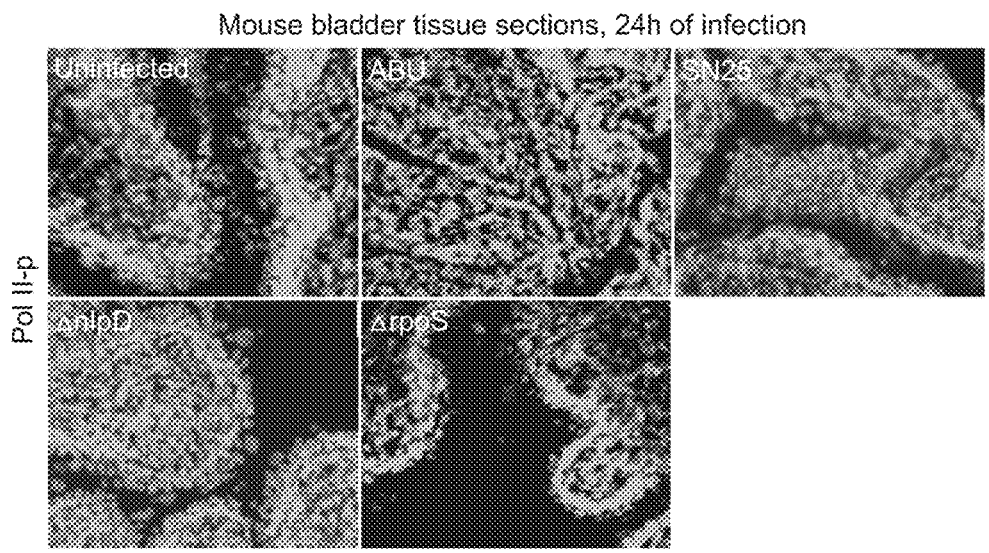
FIG. 7A-C. Functional relevance confirmed with in vivo data.
Figure 7B:
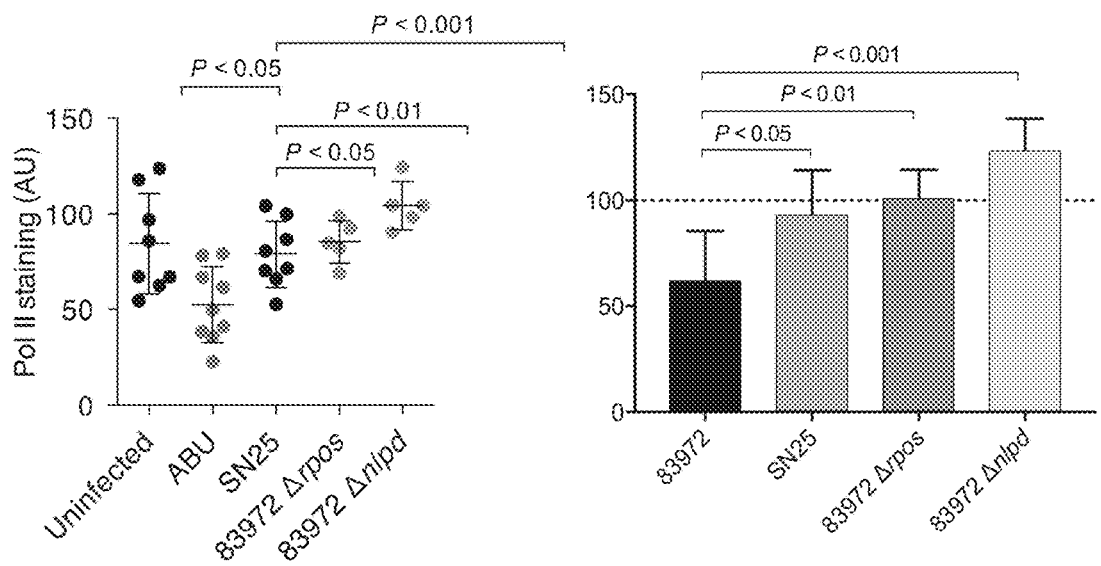
Figure 7C:
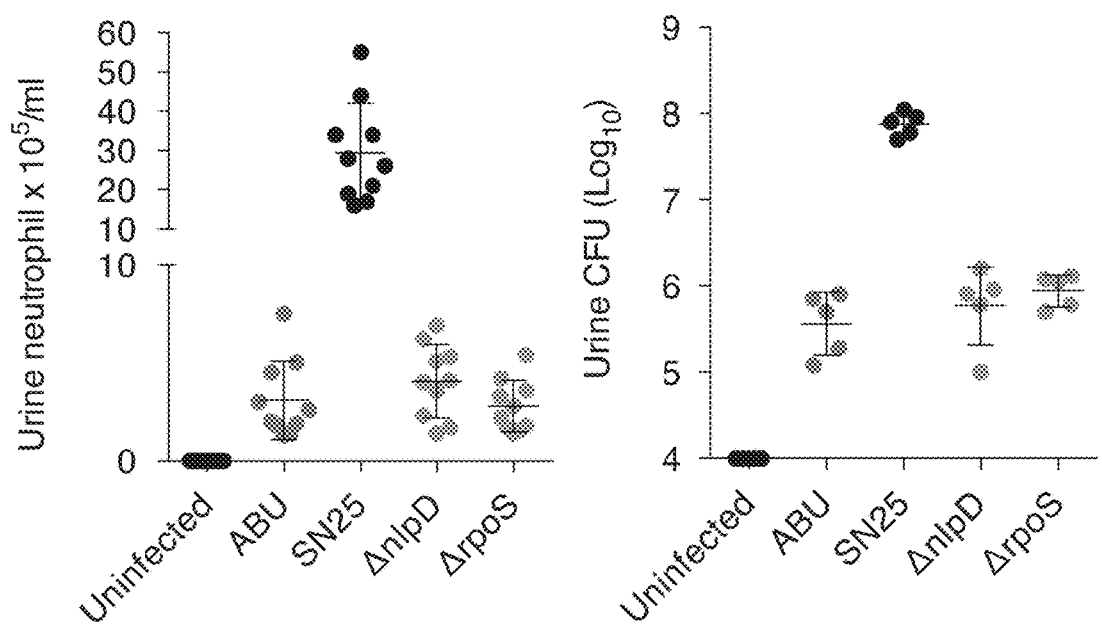

The effects on Pol II phosphorylation were confirmed in vivo, in the murine urinary tract infection model. C57BL/6 WT mice were inoculated with $2 \times 10^5$ CFU/mL of ABU 83972, SN25, delta-nlpD or delta-rpoS and sacrificed after 24 hours. Tissue levels of RNA Pol II were quantified by staining of frozen tissue sections after staining with specific antibodies (FIG. 7A). *E. coli* 83972 inhibited mucosal Pol II staining in the urinary bladder mucosa, confirming the cellular studies (p<0.05, FIG. 7B). This inhibitory effect was not detected in mice infected with the SN25 mutant strain or the delta NlpD or Sigma S mutant strains. Neutrophil counts in urine of infected mice were measured (FIG. 7C) and higher counts were found in SN25 infected mice, indicating functional relevance of Pol II de-repression. Furthermore, it was found that the SN25 infection led to higher level of bacteria in bladder, suggesting higher virulence.

Materials and Methods

Bacterial Strains

Asymptomatic bacteriuria (ABU) strain was isolated during a study of childhood UTI in Goteborg, Sweden (Lindberg et al., 1978). Bacteria were cultured on tryptic soy agar (TSA, 16 h, 37° C.) and harvested in phosphate-buffered saline (PBS, pH 7.2). For the course of infection, bacteria were diluted to reach final concentration in medium $1 \times 10^8$ cfu/ml.

Cell Culture

Human kidney carcinoma (A498, ATCC HTB44) were cultured in RPMI-1640 (Thermo Scientific) supplemented with 1 mM sodium pyruvate, 1 mM non-essential amino acids (GE Healthcare) and 10% heat-inactivated FBS at 37° C. with 5% $CO_2$.

Preparation of Bacterial Supernatant

Bacteria were incubated for 4 hours in tissue culture medium, the medium was harvested, centrifuged at 4,000×g for 10 min and filtered to remove remaining bacteria. Human kidney cells A498 were incubated with filtered supernatant for 4 hours.

Cell Flow Cytometry

Before infection, A498 cells were washed twice with RPMI medium without FCS. Cells were detached with Versene for 15 min, centrifuged at 400 g for 5 min and re-suspended in ice-cold PBS. 5×10⁵ cells were treated in suspension as follows: cells were infected, fixed (3.7% formaldehyde in PBS, 15 min), permeabilized (0.25% Triton X-100, 5% FBS in PBS, 10 min), blocked (5% FBS, 1 h at RT), incubated with primary antibodies in 5% FBS overnight at 4° C. (anti-RNA Polymerase II subunit B1 (phospho CTD Ser-2) 1:800, Merck) and with fluorescently labeled secondary antibody (Alexa Fluor® 488 goat anti-rat IgG, A-11006, 1:600, Thermo Scientific) for 1 h at RT. After each step above apart from permeabilization and blocking, cells were washed twice with ice-cold PBS and centrifuged at 400 g for 5 min. After final wash, cells were re-suspended in flow cytometry buffer 0.02% EDTA 5% FCS in PBS. With BD Accuri C6 flow cytometer (BD Biosciences), 20,000 events were collected at 60 ul/min flow rate.

Confocal Microscopy

Cells were grown to 70-80% confluence on 8-well chamber Permanox® slides (3×10⁴ cells/well, Thermo Fisher Scientific), and infected, fixed, permeabilized and treated with AB as for flow cytometry. After nuclear staining (15 min, DRAQ5, Abcam), slides were mounted (Fluoromount, Sigma-Aldrich), imaged by laser-scanning microscopy (LSM800, Carl Zeiss) and quantified by ImageJ software 1.46r (NIH).

Ion Exchange Chromatography

Organic acids were analyzed on a Dionex anion chromatography system by the Swedish Environmental Research Institute. Potassium hydroxide was used as an eluent to separate ions in the sample. To obtain the best possible separation the concentration of the eluent was gradually changed during the process. After separation, a cation exchanger was used to reduce the conductivity of the eluent and to convert the anions into their respective acids.

Global Gene Expression

Total RNA was extracted from A498 cells in RLT buffer with 1% β-Mercaptoethanol. 100 ng of RNA was amplified using GeneChip 3'IVT Express Kit, 6 ng of fragmented and labeled aRNA was hybridized onto Human Genome array strips for 16 hours at 45° C., washed, stained and scanned using the GeneAtlas system (Affymetrix). All samples passed the internal quality controls included in the array strips (signal intensity by signal to noise ratio; hybridization and labeling controls; sample quality by GAPDH signal and 3'-5' ratio <3).

Fold change was calculated by comparing cells treated with ABU or mutants to uninfected cells (PBS control) of the same genetic background. Significantly altered genes were sorted by relative expression (2-way ANOVA model using Method of Moments, P-values <0.05 and absolute fold change >1.41) (Eisenhart 1947). Heat-maps were constructed with Excel. Differentially expressed genes and regulated pathways were analyzed by Ingenuity Pathway Analysis software (IPA, Ingenuity Systems, Qiagen) and String and David open source software.

Western Blotting

Cells were lysed with RIPA lysis buffer, supplemented with protease and phosphatase inhibitors (both from Roche Diagnostics). Proteins were run on SDS-PAGE (3-8% or 4-12% Bis-Tris gels, Invitrogen), blotted onto PVDF membranes (GE Healthcare) blocked with 5% non-fat dry milk (NFDM), incubated with primary antibody: mouse anti-CDK12 (1:400 in 5% NFDM, ab9722, Abcam), mouse anti-Parafibromin (1:400 in 5% BSA, sc-22514-R, Santa Cruz), washed with PBS tween 0.1% and incubated with secondary antibodies in 5% NFDM (goat anti-mouse-HRP, Cell Signaling). Bands were imaged using ECL Plus detection reagent (GE Health Care) and quantified using ImageJ. GAPDH (1:1,000, sc-25778, Santa Cruz) was used as loading control.

The invention claimed is:

1. A method for providing immunosuppression, anti-inflammatory, or anti-infection therapy to a patient in need therefore, the method comprising administering to the patient a pharmaceutical composition comprising an effective amount of an inhibitor of RNA polymerase II, wherein said inhibitor is
   (a) an *E. coli* NlpD protein; or
   (b) an active variant of an *E. coli* NlpD protein having an amino acid sequence having at least 80% sequence identity to SEQ ID NO: 4; or
   (c) an *E. coli* Sigma S protein; or
   (d) an active variant of an *E. coli* Sigma S protein having an amino acid sequence having at least 80% sequence identity to SEQ ID NO: 1, SEQ ID NO: 2 or SEQ ID NO: 3; or
   (e) an active fragment of (a), (b), (c), or (d).

2. The method of claim 1, wherein the inhibitor of RNA polymerase II is a Sigma S protein or a variant thereof.

3. The method of claim 2, wherein the Sigma S protein or variant thereof has at least 90% sequence identity to an amino acid sequence as specified in SEQ ID NO 1, SEQ ID NO 2, or SEQ ID NO 3.

4. The method of claim 2, wherein the Sigma S protein or variant thereof has an amino acid sequence as specified in SEQ ID NO 1, SEQ ID NO 2, or SEQ ID NO 3.

5. The method of claim 1, wherein the inhibitor of RNA polymerase II is an NlpD protein or a variant thereof.

6. The method of claim 5, wherein the NlpD protein or variant thereof has at least 90% sequence identity to an amino acid sequence as specified in SEQ ID NO 4.

7. The method of claim 5, wherein the NlpD protein or variant thereof has an amino acid sequence as specified in SEQ ID NO 4.

8. The method of claim 1, wherein the inhibitor of RNA polymerase II is less than 3 kDa in molecular weight.

9. The method of claim 1, wherein the inhibitor of RNA polymerase II is a synthetic peptide.

10. The method of claim 1, wherein the inhibitor of RNA polymerase II is a recombinant peptide.

11. The method of claim 1, wherein the administering comprises oral administration, parenteral administration, or topical administration.

12. The method of claim 1, wherein the pharmaceutical composition comprises at least one pharmaceutically acceptable carrier.

13. The method of claim 1, wherein active variant of (b) and the active variant of (d) comprise only conservative amino acid substitutions relative to the *E. coli* NlpD or *E. coli* Sigma S protein, respectively.

14. The method of claim 1, wherein the amino acid sequence of the active variant of (b) has at least 95% sequence identity to SEQ ID NO: 4.

15. The method of claim 1, wherein the amino acid sequence of the active variant of (d) has at least 95% sequence identity to SEQ ID NO: 1, SEQ ID NO: 2 or SEQ ID NO: 3.

\* \* \* \* \*

SEQUENCE LISTING

```
<160> NUMBER OF SEQ ID NOS: 4

<210> SEQ ID NO 1
<211> LENGTH: 330
<212> TYPE: PRT
<213> ORGANISM: Escherichia coli
<220> FEATURE:
<223> OTHER INFORMATION: Sigma S protein

<400> SEQUENCE: 1

Met Ser Gln Asn Thr Leu Lys Val His Asp Leu Asn Glu Asp Ala Glu
1               5                   10                  15

Phe Asp Glu Asn Gly Val Glu Val Phe Asp Glu Lys Ala Leu Val Glu
            20                  25                  30

Gln Glu Pro Ser Asp Asn Asp Leu Ala Glu Glu Leu Leu Ser Gln
        35                  40                  45

Gly Ala Thr Gln Arg Val Leu Asp Ala Thr Gln Leu Tyr Leu Gly Glu
    50                  55                  60

Ile Gly Tyr Ser Pro Leu Leu Thr Ala Glu Glu Glu Val Tyr Phe Ala
65                  70                  75                  80

Arg Arg Ala Leu Arg Gly Asp Val Ala Ser Arg Arg Arg Met Ile Glu
                85                  90                  95

Ser Asn Leu Arg Leu Val Val Lys Ile Ala Arg Arg Tyr Gly Asn Arg
            100                 105                 110

Gly Leu Ala Leu Leu Asp Leu Ile Glu Glu Gly Asn Leu Gly Leu Ile
        115                 120                 125
```

-continued

Arg Ala Val Glu Lys Phe Asp Pro Glu Arg Gly Phe Arg Phe Ser Thr
          130                 135                 140

Tyr Ala Thr Trp Trp Ile Arg Gln Thr Ile Glu Arg Ala Ile Met Asn
145                 150                 155                 160

Gln Thr Arg Thr Ile Arg Leu Pro Ile His Ile Val Lys Glu Leu Asn
              165                 170                 175

Val Tyr Leu Arg Thr Ala Arg Glu Leu Ser His Lys Leu Asp His Glu
              180                 185                 190

Pro Ser Ala Glu Glu Ile Ala Glu Gln Leu Asp Lys Pro Val Asp Asp
          195                 200                 205

Val Ser Arg Met Leu Arg Leu Asn Glu Arg Ile Thr Ser Val Asp Thr
          210                 215                 220

Pro Leu Gly Gly Asp Ser Glu Lys Ala Leu Leu Asp Ile Leu Ala Asp
225                 230                 235                 240

Glu Lys Glu Asn Gly Pro Glu Asp Thr Thr Gln Asp Asp Met Lys
              245                 250                 255

Gln Ser Ile Val Lys Trp Leu Phe Glu Leu Asn Ala Lys Gln Arg Glu
              260                 265                 270

Val Leu Ala Arg Arg Phe Gly Leu Leu Gly Tyr Glu Ala Ala Thr Leu
          275                 280                 285

Glu Asp Val Gly Arg Glu Ile Gly Leu Thr Arg Glu Arg Val Arg Gln
          290                 295                 300

Ile Gln Val Glu Gly Leu Arg Arg Leu Arg Glu Ile Leu Gln Thr Gln
305                 310                 315                 320

Gly Leu Asn Ile Glu Ala Leu Phe Arg Glu
              325                 330

<210> SEQ ID NO 2
<211> LENGTH: 342
<212> TYPE: PRT
<213> ORGANISM: Escherichia coli
<220> FEATURE:
<223> OTHER INFORMATION: Sigma S protein

<400> SEQUENCE: 2

Met Phe Arg Gln Gly Ile Thr Gly Arg Ser His Leu Met Ser Gln Asn
1               5                   10                  15

Thr Leu Lys Val His Asp Leu Asn Glu Asp Ala Glu Phe Asp Glu Asn
              20                  25                  30

Gly Val Glu Val Phe Asp Glu Lys Ala Leu Val Glu Glu Glu Pro Ser
          35                  40                  45

Asn Asp Leu Ala Glu Glu Glu Leu Leu Ser Gln Gly Ala Thr Gln
50                  55                  60

Arg Val Leu Asp Ala Thr Gln Leu Tyr Leu Gly Glu Ile Gly Tyr Ser
65                  70                  75                  80

Pro Leu Leu Thr Ala Glu Glu Val Tyr Phe Ala Arg Arg Ala Leu
              85                  90                  95

Arg Gly Asp Val Ala Ser Arg Arg Met Ile Glu Ser Asn Leu Arg
              100                 105                 110

Leu Val Val Lys Ile Ala Arg Arg Tyr Gly Asn Arg Gly Leu Ala Leu
          115                 120                 125

Leu Asp Leu Ile Glu Glu Gly Asn Leu Gly Leu Ile Arg Ala Val Glu
          130                 135                 140

Lys Phe Asp Pro Glu Arg Gly Phe Arg Phe Ser Thr Tyr Ala Thr Trp
145                 150                 155                 160

```
Trp Ile Arg Gln Thr Ile Glu Arg Ala Ile Met Asn Gln Thr Arg Thr
                165                 170                 175

Ile Arg Leu Pro Ile His Ile Val Lys Glu Leu Asn Val Tyr Leu Arg
                180                 185                 190

Thr Ala Arg Glu Leu Ser His Lys Leu Asp His Glu Pro Ser Ala Glu
                195                 200                 205

Glu Ile Ala Glu Gln Leu Asp Lys Pro Val Asp Val Ser Arg Met
        210                 215                 220

Leu Arg Leu Asn Glu Arg Ile Thr Ser Val Asp Thr Pro Leu Gly Gly
225                 230                 235                 240

Asp Ser Glu Lys Ala Leu Leu Asp Ile Leu Ala Asp Glu Lys Glu Asn
                245                 250                 255

Gly Pro Glu Asp Thr Thr Gln Asp Asp Asp Met Lys Gln Ser Ile Val
                260                 265                 270

Lys Trp Leu Phe Glu Leu Asn Ala Lys Gln Arg Glu Val Leu Ala Arg
                275                 280                 285

Arg Phe Gly Leu Leu Gly Tyr Glu Ala Ala Thr Leu Glu Asp Val Gly
                290                 295                 300

Arg Glu Ile Gly Leu Thr Arg Glu Arg Val Arg Gln Ile Gln Val Glu
305                 310                 315                 320

Gly Leu Arg Arg Leu Arg Glu Ile Leu Gln Thr Gln Gly Leu Asn Ile
                325                 330                 335

Glu Ala Leu Phe Arg Glu
                340

<210> SEQ ID NO 3
<211> LENGTH: 35
<212> TYPE: PRT
<213> ORGANISM: Escherichia coli

<400> SEQUENCE: 3

Trp Ile Arg Gln Thr Ile Glu Arg Ala Ile Met Asn Gln Thr Arg Thr
1               5                   10                  15

Ile Arg Leu Pro Ile His Ile Val Lys Glu Leu Asn Val Tyr Leu Arg
                20                  25                  30

Thr Ala Arg
        35

<210> SEQ ID NO 4
<211> LENGTH: 379
<212> TYPE: PRT
<213> ORGANISM: Escherichia coli
<220> FEATURE:
<223> OTHER INFORMATION: NplD protein

<400> SEQUENCE: 4

Met Ser Ala Gly Ser Pro Lys Phe Thr Val Arg Arg Ile Ala Ala Leu
1               5                   10                  15

Ser Leu Val Ser Leu Trp Leu Ala Gly Cys Ser Asp Thr Ser Asn Pro
                20                  25                  30

Pro Ala Pro Val Ser Ser Val Asn Gly Asn Ala Pro Ala Asn Thr Asn
                35                  40                  45

Ser Gly Met Leu Ile Thr Pro Pro Lys Met Gly Thr Thr Ser Thr
        50                  55                  60

Ala Gln Gln Pro Gln Ile Gln Pro Val Gln Gln Pro Gln Ile Gln Ala
65                  70                  75                  80
```

```
Thr Gln Gln Pro Gln Ile Gln Pro Met Gln Pro Val Ala Gln Gln Pro
                 85                  90                  95

Val Gln Met Glu Asn Gly Arg Ile Val Tyr Asn Arg Gln Tyr Gly Asn
            100                 105                 110

Ile Pro Lys Gly Ser Tyr Ser Gly Ser Thr Tyr Thr Val Lys Lys Gly
        115                 120                 125

Asp Thr Leu Phe Tyr Ile Ala Trp Ile Thr Gly Asn Asp Phe Arg Asp
    130                 135                 140

Leu Ala Gln Arg Asn Asn Ile Gln Ala Pro Tyr Ala Leu Asn Val Gly
145                 150                 155                 160

Gln Thr Leu Gln Val Gly Asn Ala Ser Gly Thr Pro Ile Thr Gly Gly
            165                 170                 175

Asn Ala Ile Thr Gln Ala Asp Ala Ala Glu Gln Gly Val Val Ile Lys
            180                 185                 190

Pro Ala Gln Asn Ser Thr Val Ala Val Ala Ser Gln Pro Thr Ile Thr
        195                 200                 205

Tyr Ser Glu Ser Ser Gly Glu Gln Ser Ala Asn Lys Met Leu Pro Asn
        210                 215                 220

Asn Lys Pro Thr Ala Thr Thr Val Thr Ala Pro Val Thr Val Pro Thr
225                 230                 235                 240

Ala Ser Thr Thr Glu Pro Ile Val Ser Ser Thr Ser Thr Ser Thr Pro
                245                 250                 255

Ile Ser Thr Trp Arg Trp Pro Thr Glu Gly Lys Val Ile Glu Thr Phe
            260                 265                 270

Gly Ala Ser Glu Gly Gly Asn Lys Gly Ile Asp Ile Ala Gly Ser Lys
            275                 280                 285

Gly Gln Ala Ile Ile Ala Thr Ala Asp Gly Arg Val Val Tyr Ala Gly
        290                 295                 300

Asn Ala Leu Arg Gly Tyr Gly Asn Leu Ile Ile Ile Lys His Asn Asp
305                 310                 315                 320

Asp Tyr Leu Ser Ala Tyr Ala His Asn Asp Thr Met Leu Val Arg Glu
                325                 330                 335

Gln Gln Glu Val Lys Ala Gly Gln Lys Ile Ala Thr Met Gly Ser Thr
            340                 345                 350

Gly Thr Ser Ser Thr Arg Leu His Phe Glu Ile Arg Tyr Lys Gly Lys
        355                 360                 365

Ser Val Asn Pro Leu Arg Tyr Leu Pro Gln Arg
        370                 375
```